(12) United States Patent
Sarkas et al.

(10) Patent No.: US 10,590,278 B2
(45) Date of Patent: Mar. 17, 2020

(54) COATED POWDERS HAVING HIGH PHOTOSTABILITY

(71) Applicants: Harry W. Sarkas, Shorewood, IL (US); Abigail R. Hooper, Braidwood, IL (US); Nathan H. Hoffmann, New Lenox, IL (US)

(72) Inventors: Harry W. Sarkas, Shorewood, IL (US); Abigail R. Hooper, Braidwood, IL (US); Nathan H. Hoffmann, New Lenox, IL (US)

(73) Assignee: Nanophase Technologies Corporation, Romeoville, IL (US)

( * ) Notice: Subject to any disclaimer, the term of this patent is extended or adjusted under 35 U.S.C. 154(b) by 0 days.

(21) Appl. No.: 15/483,669

(22) Filed: Apr. 10, 2017

(65) Prior Publication Data

US 2018/0291210 A1    Oct. 11, 2018

(51) Int. Cl.

| | |
|---|---|
| *C09C 3/10* | (2006.01) |
| *C09C 1/36* | (2006.01) |
| *C09C 1/04* | (2006.01) |
| *C09C 3/06* | (2006.01) |
| *C09C 3/08* | (2006.01) |
| *A61K 8/02* | (2006.01) |
| *A61K 8/27* | (2006.01) |
| *A61K 8/29* | (2006.01) |
| *A61K 8/25* | (2006.01) |
| *A61K 8/58* | (2006.01) |
| *A61K 8/891* | (2006.01) |
| *A61Q 17/04* | (2006.01) |
| *A61Q 19/08* | (2006.01) |
| *C09K 15/08* | (2006.01) |

(52) U.S. Cl.
CPC .............. *C09C 3/10* (2013.01); *A61K 8/0241* (2013.01); *A61K 8/25* (2013.01); *A61K 8/27* (2013.01); *A61K 8/29* (2013.01); *A61K 8/585* (2013.01); *A61K 8/891* (2013.01); *A61Q 17/04* (2013.01); *A61Q 19/08* (2013.01); *C09C 1/043* (2013.01); *C09C 1/3684* (2013.01); *C09C 3/063* (2013.01); *C09C 3/08* (2013.01); *C09K 15/08* (2013.01); *A61K 2800/621* (2013.01); *A61K 2800/623* (2013.01); *A61K 2800/624* (2013.01); *C01P 2004/64* (2013.01); *C01P 2006/12* (2013.01)

(58) Field of Classification Search
None
See application file for complete search history.

(56) References Cited

U.S. PATENT DOCUMENTS

| | | |
|---|---|---|
| 2,885,366 A | 5/1959 | Iler |
| 2,938,009 A | 5/1960 | Lucas |
| 3,024,126 A | 3/1962 | Brown |
| 3,437,502 A | 4/1969 | Werner |
| 3,562,153 A | 2/1971 | Tully et al. |
| 3,635,743 A | 1/1972 | Smith |
| 3,647,742 A | 3/1972 | Stevens, Jr. |
| 3,649,588 A | 3/1972 | Kennedy-Skipton |
| 3,671,484 A | 6/1972 | Cooper et al. |
| 3,816,152 A | 6/1974 | Yates |
| 3,849,152 A | 11/1974 | Mimeault |
| 3,905,936 A | 9/1975 | Hawthorne |
| 3,920,865 A | 11/1975 | Laufer et al. |
| 3,948,676 A | 4/1976 | Laufer |
| 4,061,503 A | 12/1977 | Berger et al. |
| 4,068,024 A | 1/1978 | Laufer |
| 4,141,751 A | 2/1979 | Moreland |
| 4,151,154 A | 4/1979 | Berger |
| 4,233,366 A | 11/1980 | Sample, Jr. et al. |
| 4,243,692 A | 1/1981 | Scholze et al. |
| 4,271,234 A | 6/1981 | Schonafinger et al. |
| 4,454,288 A | 6/1984 | Lee et al. |
| 4,556,175 A | 12/1985 | Motoyama et al. |
| 4,574,082 A | 3/1986 | Tietjen et al. |
| 4,644,077 A | 2/1987 | Gupta |
| 4,781,942 A | 11/1988 | Leyden et al. |
| 4,818,614 A | 4/1989 | Fukui et al. |
| 4,845,054 A | 7/1989 | Mitchener |
| 4,877,604 A | 10/1989 | Schlossman |
| 4,882,225 A | 11/1989 | Fukui et al. |
| 4,927,464 A | 5/1990 | Cowie |

(Continued)

FOREIGN PATENT DOCUMENTS

| | | |
|---|---|---|
| AU | 2005229834 | 7/2008 |
| AU | 2005229834 | 1/2009 |

(Continued)

OTHER PUBLICATIONS

Jacobsen, A.E. et al., "Titanium dioxide pigments: Correlation between photochemical reactivity and chalking", Industrial and Engineering Chemistry, vol. 41, No. 3, pp. 523-526, (1949).
Brinker, et al., "Sol-Gel Science, The physics and chemistry of sol-gel processing", Academic press, chapters 3 and 4, pp. 97-301, (1990).
Supplementary European Search Report in corresponding European Patent Application No. 05760444.9-2011, dated May 15, 2009.
International Search Report dated Dec. 5, 2006 for PCT Application No. PCT/US05/10669.
Kinsley, Jr., G.R. "Properly purge and inert storage vessels", Chemical Engineering Progress, vol. 97, No. 2, pp. 57-61, (2001).
Baldyga, J. et al., "Effects of fluid motion and mixing on particle agglomeration and coating during precipitation", Chemical Engineering Science, vol. 60, issues 8-9, pp. 2167-2178, (2005).

(Continued)

*Primary Examiner* — Nicole P Babson
(74) *Attorney, Agent, or Firm* — Evan Law Group LLC (57) ABSTRACT

A coated powder comprises (a) particles, and (b) a coating on the surface of the particles including (1) silica moieties, (2) organo oxysilane moieties selected from the group consisting of mono-organo oxysilane moieties, bi-organo oxysilane moieties and tri-organo oxysilane moieties, and (3) poly(dialkyl)siloxane moieties. The amount by weight in $SiO_2$ equivalents of the organo oxysilane moieties and the silica moieties is at least 0.0625% of the total coated powder weight per $m^2/g$ of the specific surface area of the particle to be coated.

19 Claims, 2 Drawing Sheets

(56) References Cited

U.S. PATENT DOCUMENTS

| | | | |
|---|---|---|---|
| 5,035,803 | A | 7/1991 | Cohen |
| 5,063,254 | A | 11/1991 | Nakos |
| 5,068,056 | A | 11/1991 | Robb |
| 5,070,175 | A | 12/1991 | Tsumura et al. |
| 5,143,722 | A | 9/1992 | Hollenberg et al. |
| 5,274,064 | A | 12/1993 | Sarkar |
| 5,277,888 | A | 1/1994 | Baron et al. |
| 5,310,578 | A | 5/1994 | Thurn-Muller et al. |
| 5,328,683 | A | 7/1994 | Harashima |
| 5,348,760 | A | 9/1994 | Parker et al. |
| 5,411,761 | A | 5/1995 | Inokuchi et al. |
| 5,440,001 | A | 8/1995 | Griswold et al. |
| 5,486,631 | A | 1/1996 | Mitchnick et al. |
| 5,536,492 | A | 7/1996 | Mitchnick et al. |
| 5,562,897 | A | 10/1996 | Mitchnick et al. |
| 5,565,591 | A | 10/1996 | Mitchnick et al. |
| 5,607,994 | A | 3/1997 | Tooley et al. |
| 5,631,310 | A | 5/1997 | Tooley et al. |
| 5,674,624 | A | 10/1997 | Miyazaki et al. |
| 5,679,402 | A | 10/1997 | Lee |
| 5,718,907 | A | 2/1998 | Labarre |
| 5,756,788 | A | 5/1998 | Mitchnick et al. |
| 5,843,525 | A | 12/1998 | Shibasaki et al. |
| 5,868,959 | A | 2/1999 | Mayo et al. |
| 5,959,004 | A | 9/1999 | Tooley et al. |
| 5,993,967 | A | 11/1999 | Brotzman, Jr. et al. |
| 6,022,404 | A | 2/2000 | Ettlinger et al. |
| 6,033,781 | A | 3/2000 | Brotzman, Jr. et al. |
| 6,045,650 | A | 4/2000 | Mitchnick et al. |
| 6,066,327 | A | 5/2000 | Gubernick et al. |
| 6,086,668 | A | 7/2000 | Farneth et al. |
| 6,177,414 | B1 | 1/2001 | Tomelia et al. |
| 6,214,106 | B1 | 4/2001 | Weber et al. |
| 6,500,415 | B2 | 12/2002 | Ishii et al. |
| 6,599,631 | B2 | 7/2003 | Kambe et al. |
| 7,052,777 | B2 | 5/2006 | Brotzman, Jr. et al. |
| 7,182,938 | B2 | 2/2007 | Andre et al. |
| 7,303,819 | B2 | 12/2007 | Brotzman, Jr. |
| 7,407,666 | B2 | 8/2008 | Tarletsky et al. |
| 7,438,836 | B2 | 10/2008 | Michael et al. |
| 7,723,443 | B1 | 5/2010 | O'Lenick et al. |
| 7,790,813 | B2 | 9/2010 | O'Lenick et al. |
| 7,915,330 | B2 | 3/2011 | Bonda et al. |
| 9,139,737 | B1 * | 9/2015 | Shah ............... C09C 3/12 |
| 9,657,183 | B2 | 5/2017 | Shah et al. |
| 2005/0222325 | A1 | 10/2005 | Brotzman, Jr. |
| 2005/0255057 | A1 | 11/2005 | Andre et al. |
| 2006/0167138 | A1 | 7/2006 | Ishii et al. |
| 2006/0210495 | A1 | 9/2006 | Meyer et al. |
| 2008/0057130 | A1 | 3/2008 | Brotzman, Jr. |
| 2016/0040019 | A1 | 2/2016 | Shah et al. |
| 2017/0283628 | A1 | 10/2017 | Shah et al. |
| 2018/0291210 | A1 | 10/2018 | Sarkas et al. |

FOREIGN PATENT DOCUMENTS

| | | |
|---|---|---|
| CA | 2010790 | 2/1990 |
| CA | 2563085 | 3/2013 |
| CA | 2563085 | 11/2013 |
| DE | 2828659 | 2/1979 |
| EP | 0 389 138 | 9/1990 |
| EP | 0 558 032 | 2/1993 |
| EP | 0 665 004 | 8/1995 |
| EP | 97 919 963.5 | 4/1999 |
| EP | 97 919 963.5 | 1/2001 |
| EP | 97 919 963.5 | 5/2003 |
| EP | 0 761 774 | 7/2003 |
| EP | 05760444.9 | 5/2009 |
| EP | 2 141 205 | 1/2010 |
| EP | 09168614.7 | 6/2010 |
| EP | 05760444.9 | 4/2011 |
| EP | 05 760 444.9 | 7/2014 |
| EP | 05 760 444.9 | 5/2016 |
| EP | 05760444.9 | 1/2017 |
| EP | 15 754 058.4 | 1/2018 |
| EP | 15754058.4 | 6/2018 |
| GB | 785393 | 10/1957 |
| GB | 825404 | 12/1959 |
| GB | 2217987 | 11/1989 |
| JP | 62-016408 | 1/1987 |
| JP | 03-081209 | 4/1991 |
| JP | 4-178428 | 6/1992 |
| JP | 5-221640 | 8/1993 |
| JP | 5-306338 | 11/1993 |
| JP | 06-087714 | 3/1994 |
| JP | 6-279589 | 10/1994 |
| JP | 7-157562 | 6/1995 |
| JP | 7-165921 | 6/1995 |
| JP | 9-536259 | 11/2004 |
| JP | 9-536259 | 5/2006 |
| JP | 2006-248645 | 4/2008 |
| JP | 2007-507365 | 12/2009 |
| WO | 1990/06103 | 6/1990 |
| WO | 1990/09777 | 9/1990 |
| WO | 1995/23192 | 8/1995 |
| WO | PCT/US97/05179 | 8/1997 |
| WO | 1997/38041 | 10/1997 |
| WO | PCT/US97/05179 | 3/1998 |
| WO | 2005/098910 | 10/2005 |
| WO | PCT/US05/10669 | 12/2006 |
| WO | PCT/US05/10669 | 2/2008 |
| WO | 2009/131910 | 10/2009 |
| WO | PCT/US2015/042317 | 4/2016 |
| WO | 2017/019026 | 2/2017 |
| WO | PCT/US2015/042317 | 2/2018 |
| WO | PCT/US2018/026855 | 7/2018 |

OTHER PUBLICATIONS

Solomon, D.H. et al., "Titania Pigments" "Surface modification of pigments and filters" "Organic reactions catalyzed by mineral surfaces", chemistry of Pigments and Fillers, John Wiley & Sons, (1983).

International Search Report dated Aug. 4, 1997 for PCT Application No. PCT/US97/05179.

International Cosmetic Ingredient Dictionary, 5$^{th}$ edition, Published by the Cosmetic, Toiletry, and Fragrance Association, vol. 1, p. 401, (1993).

International Cosmetic Ingredient Dictionary, 5$^{th}$ edition, Published by the Cosmetic, Toiletry, and Fragrance Association, vol. 1, pp. 649-650, (1993).

International Cosmetic Ingredient Dictionary, 5$^{th}$ edition, Published by the Cosmetic, Toiletry, and Fragrance Association, vol. 2, p. 924, (1993).

Kingery, W.D. et al., "Introduction to Ceramics", 2$^{nd}$ Edition, John Wiley & Sons, pp. 3, 16-20, (1976).

Rompp Lexikon Chemie, 10, Auflage, pp. 4564-4565, (1999).

Rompp Lexikon Chemie, 10, Auflage, pp. 5076, (1999).

Odian, G. "Principles of Polymerization", 2$^{nd}$ Edition, John Wiley & Sons, pp. 238-239 400-401 424-425, (1981).

Billmeyer, Jr., F.W. Textbook of Polymer Science, Interscience Publishers, pp. 332-337, (1962).

Jastrzebski, Z.D. "Ceramics and Related Materials", Nature and Properties of Engineering Materials, John Wiley & Sons, Inc. p. 281, (1959).

Billmeyer, Jr., F.W. Textbook of Polymer Science, Interscience Publishers, p. 350, (1971).

Odian, G. "Principles of Polymerization", 2$^{nd}$ Edition, John Wiley & Sons, pp. 429-430, (1981).

Flory, P.J. "Nonlinearity in the macro-structure of vinyl polymers", Principles of Polymer Chemistry, Cornell University Press, Chapter III and Chapter VI, section 4, pp. 69-105, 256-262, (1971).

Meakin, P. "Models for colloidal aggregation", Annual Reviews Physical Chemistry, vol. 39, pp. 237-267, (1988).

Brinker, et al., "Sol-Gel Science, The physics and chemistry of sol-gel processing", Academic press, chapters 1, pp. 1-8, (1990).

Kingery, W.D. et al., "Introduction to Ceramics", 2$^{nd}$ Edition, John Wiley & Sons, pp. 61-71, (1976).

International Search Report and Written Opinion dated Apr. 28, 2016 for PCT Application No. PCT/US2015/042317.

(56) References Cited

OTHER PUBLICATIONS

International Search Report and Written Opinion dated Jul. 19, 2018 for PCT Application No. PCT/US2018/026855.
Jung, K. et al., "The antioxidative power AP—A new quantitative time dependent (2D) parameter for the determination of the antioxidant capacity and reactivity of different plants", Spectrochimica Acta Part A: Molecular and Biomolecular Spectroscopy, vol. 63, pp. 845-850, (2006).
Jung, K. et al., "How active are biocosmetic ingredients?", SÖFW-Journal, vol. 133, No. 1/2, pp. 1-7, (2007).
Andersch Björkman, Y. et al., "Air-oxidized linalool elicits eczema in allergic patients—a repeated open application test study", Contact Dermatitis, vol. 70, No. 3, pp. 129-138, (2014).
Jung, K. et al., "High levels of free radicals in suncare products induce acne aestivalis in sensitive subjects", SÖFW, vol. 142, pp. 2-8, (2016).
Wlaschek, M. et al., "Solar UV irradiation and dermal photoaging", Journal of Photochemistry and Photobiology B: Biology, vol. 63, issues 1-3, pp. 41-51, (2001).
Wada, N. et al., "Mycosporine-like amino acids and their derivatives as natural antioxidants", Antioxidants, vol. 4, pp. 603-646, (2015).
Vadlapudi, V. "Antioxidant activities of marine algae: A review", Medicinal Plants as Antioxidant Agents: Understanding Their Mechanism of Action and Therapeutic Efficacy, pp. 189-203, (2012).
Hanson, K.M. et al., "Bioconvertible vitamin antioxidants improve sunscreen photoprotection against UV-induced reactive oxygen species", Journal of Cosmetic Science, vol. 54, pp. 589-598, (2003).
Chisvert, A. et al., "An overview of the analytical methods for the determination of organic ultraviolet filters in biological fluids and tissues", Analytica Chimica Acta, vol. 752, pp. 11-29, (2012).
Leite-Silva et al., "Human skin penetration and local effects of topical nano zinc oxide after occlusion and barrier impairment", European Journal of Pharmaceutics and Biopharmaceutics, vol. 104, pp. 140-147, (2016).
Holmes, A.M. et al., "Relative penetration of zinc oxide and zinc ions into human skin after application of different zinc oxide formulations", ACS Nano, vol. 10, pp. 1810-1819, (2016).
Australian Government, "Literature review on the safety of titanium dioxide and zinc oxide nanoparticles in sunscreens", Department of Health, Therapeutic Goods Administration, Scientific Review Report, pp. 1-24, (2016).
EP Search Report dated Jul. 3, 2018 for EP application No. 18162675.5, 8 pages.
Matts, P.J. et al., "The COLIPA in vitro UVA method: a standard and reproducible measure of sunscreen UVA protection", International Journal of Cosmetic Science, vol. 32, issue 1, pp. 35-46, (2010).
International Standard, "Determination of sunscreen UVA photoprotection in vitro", ISO 24443, First edition, pp. 1-28, (2012).
U.S. Appl. No. 15/491,913, dated Aug. 6, 2019, 13 pages.
U.S. Appl. No. 15/917,470, dated Aug. 21, 2019, 3 pages.
U.S. Appl. No. 11/923,169, dated Jun. 23, 2010, 16 pages.
U.S. Appl. No. 11/923,169, dated Sep. 29, 2009, 9 pages.
U.S. Appl. No. 11/076,128, dated Jul. 26, 2007, 9 pages.
U.S. Appl. No. 11/076,128, dated Oct. 2, 2006, 8 pages.
U.S. Appl. No. 08/827,229, dated Jul. 15, 1998, 9 pages.
U.S. Appl. No. 08/827,229, dated Apr. 13, 1999, 4 pages.
U.S. Appl. No. 08/827,229, dated Oct. 7, 1999, 2 pages.
U.S. Appl. No. 08/954,396, dated Aug. 10, 1998, 7 pages.
U.S. Appl. No. 08/954,396, dated Jul. 26, 1999, 2 pages.
U.S. Appl. No. 08/954,396, dated May 6, 1999, 5 pages.
U.S. Appl. No. 08/954,396, dated Jul. 29, 1999, 2 pages.
U.S. Appl. No. 13/301,628, dated Nov. 12, 2013, 9 pages.
U.S. Appl. No. 13/301,628, dated Apr. 10, 2014, 18 pages.
U.S. Appl. No. 13/301,628, dated Jan. 27, 2015, 14 pages.
U.S. Appl. No. 13/301,628, dated May 1, 2015, 3 pages.
U.S. Appl. No. 13/301,628, dated May 14, 2015, 11 pages.
U.S. Appl. No. 14/827,155, dated May 3, 2015, 21 pages.
U.S. Appl. No. 14/827,155, dated Jan. 11, 2017, 9 pages.
U.S. Appl. No. 14/827,155, dated Feb. 7, 2017, 6 pages.
U.S. Appl. No. 15/491,913, dated Jun. 12, 2018, 24 pages.

* cited by examiner

COATED POWDERS HAVING HIGH PHOTOSTABILITY

BACKGROUND

Particles are added to enhance and modify the properties of many different types of compositions and products. Examples include ultra-violet (UV) light absorbing particles, pigments, colorants, fillers, matting agents, optical diffusing particles, abrasion resistant particles, viscosity modifiers, magnetic particles and reflective particles.

Particles comprising oxides are particularly suitable as additives, especially particles containing zinc oxides, titanium oxides, silicon oxides, aluminum oxides, iron oxides and/or rare-earth metal oxides. These oxides are thermodynamically stable, are typically unable to react with environmentally ubiquitous oxygen, and tend to be less reactive with water than many other oxides and non-oxide materials. These oxide materials have been used as pigments and abrasives for centuries.

Particles consisting of certain metal oxides, most notably titanium oxides, are particularly interesting because they are usually colorless and transparent to visible light, and provide protection against exposure to UV light; however, they tend to have poor photostability, caused by the photocatalytic behavior of these oxides. Metal oxides exposed to UV radiation produce an increase in free radicals. These free radicals can lead to a de-stabilization of the formulation itself. Furthermore, free radicals may cause the formation of hydroperoxides and other peroxide free radicals known to induce contact dermatitis and severe allergic reactions. These free radicals also trigger chain reactions resulting in reactive oxygen species (ROS). These highly reactive derivatives react with cellular components including lipid membranes and are considered a source of photoaging and skin cancers that appear later in life. ROS deplete and damage non-enzymatic and enzymatic antioxidant defense systems and cause permanent genetic damage. Other components in a cosmetic composition may also have low photostability, producing additional free radicals on the skin surface.

Coating particles has been found to improve the photostability of particles. Coated powders are used to prepare cosmetic compositions for application to the skin, such as compositions for protecting skin from UV radiation (for example, sunscreens).

Particles can be coated to produce coated powders having chemical stability, photostability, and the ability to form a high weight loading dispersion with low viscosity. For example, a coating was found that produced chemical stability, photostability, and such coated particles may be used to form high weight loading dispersions with low viscosity. The coating comprises (1) silica moieties, (2) organo oxysilane moieties selected from the group consisting of mono-organo oxysilane moieties, bi-organo oxysilane moieties and tri-organo oxysilane moieties, and (3) poly(dialkyl)siloxane moieties. See, for example, U.S. Pat. No. 9,139,737.

Antioxidants, often used in cosmetic skin care products, undergo oxidation processes under UV radiation, losing their effectiveness. The addition of coated powders that block and absorb UV radiation may reduce the oxidation of antioxidants caused by UV radiation. However, many UV blocking particles exhibit photocatalytic activity, such as zinc oxide and titanium oxide, and can lead to the generation of peroxide free radicals inside a cosmetic composition. This may compromise the stability and efficacy of the antioxidants, due to the prompt reaction between the antioxidants and the free radicals or the products produced by the free radicals.

SUMMARY

In a first aspect, the present invention is a coated powder, comprising (a) particles, and (b) a coating, on the surface of the particles, including (1) silica moieties, (2) organo oxysilane moieties selected from the group consisting of mono-organo oxysilane moieties, bi-organo oxysilane moieties and tri-organo oxysilane moieties, and (3) poly(dialkyl)siloxane moieties. The amount by weight in $SiO_2$ equivalents of the organo oxysilane moieties and the silica moieties is at least 0.0625% of the total coated powder weight per $m^2/g$ of the specific surface area of the particle to be coated.

In a second aspect, the present invention is a dispersion, comprising (1) the coated powder, (2) a fluid, and (3) an antioxidant.

In a third aspect, the present invention is a process for producing a coated powder, comprising coating particles with a polymer, by polymerizing a composition, comprising (i) the particles, (ii) a first alkoxy silane selected from the group consisting of a tetra-alkoxy silane, a poly(tetra-alkoxy silane), and mixtures thereof, (iii) an organo alkoxysilane selected from the group consisting of mono-organo alkoxysilane, bi-organo alkoxysilane, tri-organo alkoxysilane, and mixtures thereof, and (iv) a second alkoxy silane selected from the group consisting of a poly(dialkyl)siloxane, and mixtures thereof. The amount by weight in $SiO_2$ equivalents of the organo oxysilane moieties and the silica moieties is at least 0.0625% of the total coated powder weight per $m_2/g$ of the specific surface area of the particle to be coated.

In a fourth aspect, the present invention is a coated powder which is super-photostable.

In a fifth aspect, the present invention is a method of protecting skin from light, comprising coating skin with a composition comprising the coated powder.

In a sixth aspect, the present invention is a method of protecting keratinous material comprising coating the keratinous material with a composition comprising the coated powder.

In a seventh aspect, the present invention is a method of protecting skin from light, comprising coating skin with the dispersion.

In an eighth aspect, the present invention is a method of suppressing lipid peroxidation comprising applying to the skin a composition comprising the coated powder.

In a ninth aspect, the present invention is a method of preventing or reducing lines and wrinkles on the skin comprising applying to the skin a composition comprising the coated powder.

In a tenth aspect, the present invention is a method of preventing loss of elasticity of the skin comprising applying to the skin a composition comprising the coated powder.

In an eleventh aspect, the present invention is a method of preventing thinning of the skin comprising applying to the skin a composition comprising the coated powder.

Definitions

The term "nanoparticle" means a particle having a particle size of at most 999 nm. Preferably, a nanoparticle has a particle size of 10 nm to 500 nm.

The term "microparticle" means a particle having a particle size of 1 μm to 100 μm.

The term "particle size" means the average diameter of the image of the particle as viewed by electron microscopy, unless otherwise stated. The term "average particle size" means the average of the particle sizes of a collection of particles.

"High solids content" or "high weight loading" means that the composition referred to has at least 50 wt. % solid particles.

"Alkyl" (or alkyl- or alk-) refers to a substituted or unsubstituted, straight, branched or cyclic hydrocarbon chain, preferably containing of from 1 to 22 carbon atoms. More preferred alkyl groups are lower alkyl groups, for example, alkyl groups containing from 1 to 10 carbon atoms. Preferred cycloalkyls have 3 to 10, preferably 3 to 6, carbon atoms in their ring structure. Suitable examples of unsubstituted alkyl groups include methyl, ethyl, propyl, isopropyl, cyclopropyl, butyl, iso-butyl, tert-butyl, sec-butyl, cyclobutyl, pentyl, cyclopentyl, hexyl, and cyclohexyl.

"Alkenyl" refers to a substituted or unsubstituted, straight, branched or cyclic, unsaturated hydrocarbon chain that contains at least one double bond, and preferably having 2 to 22, more preferably 2 to 6, carbon atoms. Exemplary unsubstituted alkenyl groups include ethenyl (or vinyl) (—CH=CH$_2$), 1-propenyl, 2-propenyl (or allyl) (—CH$_2$—CH=CH$_2$), 1,3-butadienyl (—CH=CHCH=CH$_2$), 1-butenyl (—CH=CHCH$_2$CH$_3$), hexenyl, pentenyl, and 1,3,5-hexatrienyl. Preferred cycloalkenyl groups contain 5 to 8 carbon atoms and at least one double bond. Examples of cycloalkenyl groups include cyclohexadienyl, cyclohexenyl, cyclopentenyl, cycloheptenyl, cyclooctenyl, cyclohexadienyl, cycloheptadienyl, and cyclooctatrienyl.

"Alkynyl" refers to a substituted or unsubstituted, straight, branched or cyclic unsaturated hydrocarbon chain containing at least one triple bond, and preferably having 2 to 22, more preferably 2 to 6, carbon atoms.

"Aryl" refers to any aromatic carbocyclic or heteroaromatic group, preferably having 3 to 10 carbon atoms. The aryl group can be cyclic (such as phenyl (or Ph)) or polycyclic (such as naphthyl) and can be unsubstituted or substituted. Preferred aryl groups include phenyl, naphthyl, furyl, thienyl, pyridyl, indolyl, quinolinyl or isoquinolinyl.

"Heterocyclic radical" refers to a stable, saturated, partially unsaturated, or aromatic ring, preferably containing 5 to 10, more preferably 5 or 6, atoms. The ring can be substituted 1 or more times (preferably 1, 2, 3, 4 or 5 times) with substituent(s). The ring can be mono-, bi-or polycyclic. The heterocyclic group consists of carbon atoms and 1 to 3 heteroatoms independently selected from the group consisting of nitrogen, oxygen, and sulfur. The heteroatoms can be protected or unprotected. Examples of useful heterocyclic groups include substituted or unsubstituted acridine, benzathiazoline, benzimidazole, benzofuran, benzothiophene, benzthiazole, benzothiophenyl, carbazole, cinnoline, furan, imidazole, 1H-indazole, indole, isoindole, isoquinoline, isothiazole, morpholine, oxazole, phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, and triazole.

"Substituted" means that the moiety contains at least one, preferably 1-3 substituent(s). Suitable substituents include hydrogen (H) and hydroxyl (—OH), amino (—NH$_2$), oxy (—O—), carbonyl (—CO—), thiol, alkyl, alkenyl, alkynyl, alkoxy, halo, nitrile, nitro, aryl, and heterocyclic groups.

The photostability of titanium dioxide (TiO$_2$) is measured using the test described below. This test is referred to as the "TiO$_2$ photostability test." First a stock solution of 25% resorcinol in ethanol is prepared. 8.9 g (±0.01 g) of Finsolv TN and 0.1 g (±0.005 g) of Hostaphat KW 340D are added to a glass scintillation vial. The capped vial is then placed in a 50° C. oven until the Hostaphat KW 340D dissolves and the solution is homogeneous (approximately 15 minutes). After removing the vial from the oven, 1.0 g (±0.01 g) of coated titanium dioxide powder is added to the solution. The solution is placed in a sonicator bath and sonicated for 15 minutes. 1.0 g (±0.01 g) of the 25% resorcinol in ethanol from the first step is added to the scintillation vial and mixed thoroughly by hand until homogenous. A quartz cuvette is filled with the mixture and capped with a Teflon lid. The mixture is then tested using a Milton Roy Color Mate Colorimeter or suitable equivalent colorimeter. Before testing the mixture, the colorimeter is calibrated using the white tile calibration standard. After recording the results of the "pre-irradiated sample", the cuvette containing the sample is placed in the QUV weatherometer. The mixtures are then exposed to UV light for exactly 15 minutes in a Q-Labs QUV weatherometer using UVB bulbs at 1.23 Wm$^{-2}$s$^{-1}$ at a constant temperature of 50° C. The test mixtures are then removed for immediate color measurement in the colorimeter. Photostability may be expressed as the total color change relative to a standard (ΔE in L*a*b* color space) for a stated UV exposure time. ΔE is calculated from the following expression, as per the CIE76 definition:

$$\Delta E = \sqrt{(L^*_2 - L^*_1)^2 + (a^*_2 - a^*_1)^2 + (b^*_2 - b^*_1)^2}$$

where $L^*_2$, $a^*_2$, and $b^*_2$ are the color coordinates of test mixture post irradiation and where $L^*_1$=99.47, $a^*_1$=−0.16, and $b^*_1$=−0.17 and correspond to the color coordinates of a white refernce tile. A coated TiO$_2$ particle is "super-photostable" if ΔE≤15 in the above photostability test.

In order to test the photostability of most compositions other than TiO$_2$, such as zinc oxide (ZnO), the following test may be used. This test is referred to as the "DPPH photostability test." First, 0.025 g±0.001 g of coated ZnO powder is added to four 50 mL disposable plastic beakers. 0.0125% DPPH (di(phenyl)-(2,4,6-trinitrophenyl) iminoazanium, also referred to as diphenylpicrylhydrazyl; CAS Number 1898-66-4) is prepared in BCS (ethylene glycol butyl ether) solution. 19.975 g±0.001 of 0.0125% DPPH in BCS solution is added to each beaker containing coated powder. This is mixed thoroughly with a glass stir rod, and each beaker is sonicated for 20 seconds, ensuring the powder is well-dispersed throughout the solution. After sonication, the sample is transferred to a labelled scintillation vial. The pre-irradiated samples are measured on a calibrated Milton Roy Color Mate Colorimeter or suitable equivalent colorimeter. After taking the measurements, the samples are irradiated. The test mixtures are then exposed to UV light in a Q-Labs QUV weatherometer using a UVA or UVB bulb at 0.35 Wm$^{-2}$s$^{-1}$ at a constant temperature of 50° C. for exactly 10 minutes. UVA bulbs are used to test particles that filter UVA radiation, and UVB bulbs are used to test particles that filter UVB radiation. Finally, the post-irradiated samples are measured on the colorimeter. In this case, photostability following UV exposure is indicated by the persistence of the purple color due to the absorption band of the dye at 520 nm. Photostability may be expressed as the total color change relative to a standard (ΔE in L*a*b* color space) for a stated UV exposure time. ΔE is calculated from the following expression, as per the CIE76 definition:

$$\Delta E = \sqrt{(L^*_2 - L^*_1)^2 + (a^*_2 - a^*_1)^2 + (b^*_2 - b^*_1)^2}$$

where $L^*_2$, $a^*_2$, and $b^*_2$ are the color coordinates of test mixture post irradiation and where $L^*_1$, $a^*_1$, and $b^*_1$ are the initial color coordinates of test mixture prior to irradiation.

Data is reported as the average ΔE value of the four samples. A coated particle is "super-photostable" if ΔE≤4.5 in the above photostability test.

The photostability of coated effects pigments is measured using a modified version of the previously described tests. This test is referred to as the "effects pigments photostability test." The modifications were necessary to remove noise in the colorimetry measurements induced by the reflectance of the interference pigments themselves in the samples. The test is described below. 0.0125% DPPH (di(phenyl)-(2,4,6-trinitrophenyl) iminoazanium, also referred to as diphenylpicrylhydrazyl; CAS Number 1898-66-4) is prepared in BCS (ethylene glycol butyl ether) solution. A 20 ml aliquot of the DPPH solution is transferred to a labelled scintillation vial. This sample is measured on the calibrated Milton Roy Color Mate Colorimeter or suitable equivalent colorimeter. Next, 0.025 g±0.001 g of coated effects pigment powder is added to four 50 mL disposable plastic beakers. 19.975 g±0.001 of 0.0125% DPPH in BCS solution is added to each beaker containing coated powder. This is mixed thoroughly with a glass stir rod, and each beaker is sonicated for 20 seconds, ensuring the powder is well-dispersed throughout the solution. After sonication, each sample is transferred to a labelled scintillation vial. The test mixtures are then exposed to UV light in a Q-Labs QUV weatherometer using UVB bulbs at 0.35 $Wm^{-2}s^{-1}$ at a constant temperature of 50° C. for exactly 10 minutes. The post-irradiated samples are then filtered through a suitable 1 μm filter to remove the effects pigments, which can interfere with the color measurement. Finally, the filtered post-radiated samples are measured on the colorimeter. As before, photostability following UV exposure is indicated by the persistence of the purple color due to the absorption band of the dye at 520 nm. Photostability may be expressed as the total color change relative to a standard (ΔE in L*a*b* color space) for a stated UV exposure time. ΔE is calculated from the following expression, as per the CIE76 definition:

$$\Delta E = \sqrt{(L^*_2 - L^*_1)^2 + (a^*_2 - a^*_1)^2 + (b^*_2 - b^*_1)^2}$$

where $L^*_2$, $a^*_2$, and $b^*_2$ are the color coordinates of test mixture post irradiation and where $L^*_1$, $a^*_1$, and $b^*_1$ are the initial color coordinates of as-made DPPH solution. Data is reported as the average ΔE value of the four samples. A coated particle is "super-photostable" if ΔE≤1.15 in the above photostability test, which represents half of the accepted just noticeable difference value based on CIE76.

Chemical reactivity is measured using the following chemical reactivity test. A 20 g glass vial is filled with 4.5 g of a stock solution of 5% n-propyl gallate (propyl 3,4,5-trihydroxybenzoate, Aldrich) in isopropyl alcohol. One half of a gram of the powder to be evaluated is added to the glass vial. The glass vial is then agitated, such as by being placed in a bath sonicator for 30 seconds. The mixture is allowed to stand for 30 minutes. The sample is then gently mixed using a pipette and transferred to a cuvette (polycarbonate, polystyrene, or glass) having a path length of 1 cm. The total color change (ΔE) is then measured against a factory white color standard using a Data Color-International Spectraflash SF3000 Colorimeter. Chemical reactivity is expressed as the total color change (ΔE). A powder is considered to be chemically reactive in application if the chemical reactivity test results in the appearance of a tan color with an accompanying ΔE value greater than 20.

Hydrophobicity is measured using the following hydrophobicity test (this test is a visible water floatation test commonly used in the cosmetics industry, and is described in U.S. Pat. No. 4,454,288). Approximately 30 mL of deionized water is placed into a glass jar. Approximately 3.0 g±0.30 g of the powder to be tested is added into the glass jar. The glass jar is tightly sealed, and the sample is swirled around 4 to 5 times and vigorously shaken 4 to 5 times, so that intimate contact between the water and the powder is achieved. The powder is considered to be hydrophobic if the powder is buoyant (floating on the surface of the water) and water is clear after 15 minutes. The sample is marginally hydrophobic if the powder is not buoyant but the water is clear after 15 minutes, or if the powder is buoyant but the water is not clear after 15 minutes.

The fluidity of dispersions of powders is measured using the following run-off distance test. Dispersions are produced at 50% solids in ethylhexyl benzoate (Finsolv® EB, Innospec). Three drops (75 mg) of the dispersion from a pipette are placed onto a clean glass plate substrate while the surface is in a horizontal position. The glass substrate is then held upright for 120 seconds at an angle of 90 degrees to allow the dispersion to flow. The fluidity of the dispersion is expressed as the distance the dispersion flows from the origin. (This test was only used during initial screening; a measured run-off distance of 164±10 mm (reported as standard error) from the origin corresponds to a viscosity of 145±25 cP (reported as standard error) at a shear rate of 20 $s^{-1}$.). A coated powder is considered to produce a pourable dispersion if at 50% solids in an ethylhexyl benzoate dispersion it shows a run-off distance exceeding 100 mm.

The viscosity of dispersions of powders is measured using the following viscosity test. Dispersions of the powders are prepared in capric/caprylic triglycerides (ALDO® MCT Special KFG, Lonza, CAS Number 73398-61-5), ethylhexyl benzoate (Finsolv® EB, Innospec), and linear alkyl benzoate (Finsolv® TN $C_{12-15}$Alkyl Benzoate CAS No.: 68411-27-8) at 50 wt % solids, unless otherwise specified. Viscosity is measured for each dispersion using a Brookfield DVIII+ Ultra Rheometer with a CP52 spindle at 25° C. Measurements are made at shear rates ranging from 0.1 $s^{-1}$ to 100 $s^{-1}$.

The specific surface area of particles is measured in $m^2/g$ and is determined using the Brunauer-Emmett-Teller (BET) method.

$SiO_2$ equivalents mean the weight of $SiO_2$ present after converting all the silicon in the coating into $SiO_2$. For example, "the amount by weight, in $SiO_2$ equivalents", of the moieties means that all the silicon that formed the coating is converted to $SiO_2$ and measured, in order to determine the percent of each moiety in the coated powder.

Antioxidative power (AP) is measured using the AP method developed by Gematria Laboratories (Berlin, Del.). This method offers determination of the overall antioxidative power of active ingredients, that is, plant extracts, vitamins etc., by monitoring the reducing activity against a stable test radical—DPPH with Electron Spin Resonance (ESR) spectroscopy. The AP method utilizes the well-known DPPH method with the major difference being that both the antioxidative capacity and the antioxidative activity are used to characterize the antioxidant being tested. For this purpose, different concentrations of the active ingredients are assayed in real time by ESR spectroscopy and the decrease of the test radical spins is tracked accordingly for each set. With this innovative technique, important kinetic information is additionally obtained that is completely neglected by most other test systems. Therefore, both the reaction time and the reduction potential of the antioxidants contribute to the calculation of the AP.

$$AP = (RA \times N \text{ spins})/(w_c \times t_r)$$

The AP may be described by the equation above, where RA is the constant reduction amplitude ($1/e^2$), N spins is the quantity of reduced free radicals characterized by free electrons (spins) of DPPH, $w_c$ is the characteristic weight of the antioxidant product and $t_r$ is the reduction time (Jung et al., 2006). The resulting AP is expressed in antioxidative units (AU), where 1 AU corresponds to the activity of a 1 ppm solution of pure vitamin C (ascorbic acid) as a benchmark. This method allows a rapid and generally applicable technique for the measurement of the AP across a range of very different classes of substances.

DETAILED DESCRIPTION

Coated powders of $TiO_2$ and other selected metal oxides would be desirable for use in UV protective topical skin compositions, and other UV protective coatings. However, in order to be commercially desirable, such coated powders need to be (a) photostable, so that they do not significantly change color during exposure to UV light; (b) not chemically reactive, so that they do not react with or discolor compositions during storage; and (c) may be formed into high weight loading dispersions which allow for high SPF values with minimal introduction of carrier fluid and for cost efficient transport and storage, but which have a viscosity low enough for easy handling and mixing when preparing consumer compositions.

Although the multifunctional coated powders and high dispersion solids described in U.S. Pat. No. 9,139,737 is a significant improvement over other existing coated powders, it could be further improved by increasing the photostability of the coated powders. Furthermore, the addition of antioxidants to UV protective compositions would reduce the amount of induced free radicals caused by UV radiation exposure.

The present application makes use of coated powders having superior photostability, in addition to being chemically stable and having the ability to be formed into high weight loading dispersions. The coated powders are superphotostable. The coated powder may be used to form compositions containing antioxidants, and which have a reduced loss of antioxidants upon exposure to light.

The coated powders are particles coated with a polymer, prepared by polymerizing a composition containing the particles and at least three components: (A) a first alkoxy silane selected from the group consisting of a tetra-alkoxy silane, a poly(tetra-alkoxy silane), and mixtures thereof, (B) an organo alkoxysilane selected from the group consisting of mono-organo alkoxysilane, bi-organo alkoxysilane, tri-organo alkoxysilane, and mixtures thereof, and (C) a second alkoxy silane selected from the group consisting of a poly (dialkyl)siloxane, and mixtures thereof.

The coating formed contains moieties corresponding with each of the three components: (A) silica moieties, (B) organo oxysilane moieties selected from the group consisting of mono-organo oxysilane moieties, bi-organo oxysilane moieties and tri-organo oxysilane moieties, and (C) poly (dialkyl)siloxane moieties. The coated powders can be used to form dispersions in cosmetically acceptable fluids which have high solids and low viscosity.

When at least a specific amount of Si (measured as $SiO_2$ weight equivalents) from all silanes is present in the coating, it has been found to yield superior photostability. The compositional range for each component is based on $SiO_2$ equivalents. $SiO_2$ derived from all silane moieties, that is, silica moieties and organo oxysilane moieties, must be greater than or equal to 0.0625% of the total coated powder weight per $m^2/g$ of specific surface area of the particle to be coated. The silane moieties may be mono, di, tri, and tetrafunctional.

The coated powders can be used to form dispersions in fluids which have high solids and low viscosity. The dispersion may be used to prepare cosmetic compositions for application to the skin, such as composition for protecting skin from UV radiation (for example, sunscreens). Materials considered to be cosmetically acceptable are those which are INCI (International Nomenclature of Cosmetic Ingredients) listed. Examples of cosmetically acceptable fluids are ethylhexyl benzoate (EB), linear alkyl benzoate (LAB), caprylic/capric triglyceride (CCT), squalane, natural product oils, and a variety of silicone fluids. Natural product oils are oils derived from seeds, beans, fruits, flowers, peels, leaves, and the like, including their derivatives. Examples of natural product oils are olive oil and soybean oil.

The coated powder, as well as the dispersions of the coated powder may be used in a variety of products. They may be added to dermatological compositions to provide UV protection to skin, especially in the case of $TiO_2$ and ZnO containing coated powders; the coated powder may also be added to such compositions as inorganic pigments. The coated powders may also be added to shampoos, lotions, gels, hairsprays, aerosol foam creams or emulsions, for washing, coloring and for styling hair, while also providing UV protection to hair. They may be added to paints, sealants and other coatings for wood, plastics and other construction materials; again, UV protection is provided in the case of $TiO_2$ and ZnO containing coated powders. They may also be added to resins, filled polymers and plastics, and inks. Magnetic fluids may be prepared when the metal oxide is magnetic, as in the case of certain iron oxides and rare-earth oxides.

The particles preferably comprise a metal oxide, for example zinc oxide, titanium oxide, silicon oxide, aluminum oxide, iron oxide, bismuth oxide, cerium oxide, rare-earth oxides, infrared light absorbing binary and ternary mixed metal oxides and mixtures thereof. Examples include ZnO, $TiO_2$, $SiO_2$, $Al_2O_3$, $Fe_2O_3$, $CeO_2$, $SnO_2$, zirconium-cerium oxides, mixed zirconium-rare earth oxides containing cerium, aluminosilicates (including amorphous aluminosilicate, crystalline aluminosilicates, and pumice) and other silicates, aluminum oxides include alumina, aluminosilicates, magnesium aluminum oxides (for example, spinel), zinc oxide doped with trivalent metal cations (including aluminum-doped ZnO), antimony-tin oxide (ATO), indium-tin oxide (ITO), fluorine doped tin oxide and doped tungsten oxides. Oxide minerals, such as micas and natural mineral oxides, may also be used. Metals, other ceramic compositions including carbides and nitrides and mixtures thereof, as well as mixtures with oxides, may also be used.

The particles may be effects pigments. The effects pigments are typically plate or plate-like pigment particles coated with thin layers of a secondary material with a higher refractive index. The compositions of the underlying plates are typically mica, synthetic mica, silica, or alumina. The coatings are typically titanium dioxide (typically anatase form), iron oxide, or bismuth oxychloride. The color of the pigments is controlled by the thickness of the coating layer. The effects pigments typically range from 1-100 µm in size. The pigments are also referred to as pearlescent pigments and interference pigments. These materials are commercially available (XIRALLIC®, PYRISMA®, COLORSTREAM® and IRIODIN® families of products from EMD Performance Materials, MEARLIN® pearlescent pigments from BASF, and SYNCRYSTAL®, SYNAFIL®, MIRAGE®, and VISIONAIRE® effects pigments from Eckart).

Preferably, the particles have a particle size of at most 999 nm, including a particle size of at most 100, 200, and 500 nm, more preferably a particle size of 10 nm to 500 nm, most preferably a particle size of 15 nm to 250 nm, such as 20, 30, 40, 50, 60, 70, 80, 90, and 100 nm. Preferably, the particles have an average particle size of at most 999 nm, including an average particle size of at most 100, 200, and 500 nm, more preferably an average particle size of 10 nm to 500 nm, most preferably an average particle size of 15 nm to 250 nm, such as 20, 30, 40, 50, 60, 70, 80, 90, and 100 nm. Alternatively, the particles may have a particle size of 1 µm to 100 µm. Preferably the particle has an average size of 1 to 10 µm.

The particles may be coated by polymerizing the composition, preferably without solvents and with at least some of the composition in the gas phase. The composition includes (A) a first alkoxy silane selected from the group consisting of a tetra-alkoxy silane, a poly(tetra-alkoxy silane), and mixtures thereof, (B) an organo alkoxysilane selected from the group consisting of mono-organo alkoxysilane, bi-organo alkoxysilane, tri-organo alkoxysilane, and mixtures thereof, and (C) a second alkoxy silane selected from the group consisting of a poly(dialkyl)siloxane, and mixtures thereof.

Preferably, the first alkoxy silane is present in an amount of 0.1 to 8% by weight of the coated powder, more preferably 0.5% to 7% by weight of the coated powder, and most preferably 1.0 to 5% by weight of the coated powder, including 1.5, 2, 2.5, 3, 3.5, 4 and 4.5%. Preferably, the organo alkoxysilane is present in an amount of 0.01 to 5% by weight of the coated particles, more preferably 0.05 to 3% by weight of the coated powder, and most preferably 0.1 to 1% by weight of the coated powder, including 0.1, 0.2, 0.3, 0.4, 0.5, 0.6, 0.7, 0.8 and 0.9%. Preferably, the second alkoxy silane is present in an amount of 0.1 to 10% by weight of the coated powder, more preferably 0.5 to 5% by weight of the coated powder, and most preferably 0.75 to 2.5% by weight of the coated powder, including 1.0, 1.25, 1.5, 1.75, 2.0 and 2.25%.

The first alkoxy silane may be a tetra-alkoxy silane, a poly(tetra-alkoxy silane), or mixtures thereof. Tetra-alkoxy silanes are compounds of the formula $(R^aO)_4Si$, where each $R^a$ is an organic group which may be the same or different, and each $R^a$ is preferably an alkyl groups having 1 to 22 carbon atoms, more preferably 1 to 10 carbon atoms, including 2, 3, 4, 5, 6, 7, 8, and 9 carbon atoms, including methyl, ethyl, and propyl. An example is tetraethoxy silane (TEOS). A poly(tetra-alkoxy silane) is an oligomer of one or more tetra-alkoxy silanes, formed by partial hydrolysis. Preferably the poly(tetra-alkoxy silane) contains 2 to 14 monomer units, more preferably 4 to 10 monomer units, including 5, 6, 7, 8, and 9.

The first alkoxy silane may contain silica moieties. Silica moieties are $Si(O)_4$ groups which bond to 4 atoms, and may also be present in clusters such as $[OSi(O_2)]_nO$, where n is 2 to 14, more preferably 4 to 10, including 5, 6, 7, 8 and 9.

The organo alkoxysilane is selected from the group consisting of mono-organo alkoxysilane, bi-organo alkoxysilane, tri-organo alkoxysilane, and mixtures thereof. The organo alkoxysilane are compounds of the formula $R^1{}_nSi(OR^b)_{4-n}$ where n is 1, 2 or 3. $R^1$ is an organic group, such as alkyl (for example, linear alkyl, branched alkyl, cyclic alkyl, glycidoxyalkyl, methancryloxyalkyl and aminoalkyl), aryl, vinyl and heteroaryl. Examples of $R^1$ include methyl, ethyl, propyl, butyl, pentyl, hexyl, heptyl, octyl, nonyl, decyl, dodecyl, tridecyl, tetradecyl, pentadecyl, hexadecyl, heptadecyl, and octadecyl. Preferably, $R^1$ contains 1 to 22 carbon atoms, more preferably 1 to 10 carbon atoms, including 2, 3, 4, 5, 6, 7, 8 and 9 carbon atoms. Each $R^b$ is an organic group which may be the same or different, and each $R^b$ is preferably an alkyl groups having 1 to 22 carbon atoms, more preferably 1 to 10 carbon atoms, including 2, 3, 4, 5, 6, 7, 8 and 9 carbon atoms, including methyl, ethyl, and propyl. An example of an organo alkoxysilane is triethoxy octylsilane.

The organo alkoxysilane may contain organo oxysilane moieties. Organo oxysilane moieties are $R^1{}_nSi(O)_{4-n}$ groups which bond to "4-n" other atoms, where n is an integer of 1, 2 or 3. $R^1$ is an organic group, such as alkyl (for example, linear alkyl, branched alkyl, cyclic alkyl, glycidoxyalkyl, methancryloxyalkyl and aminoalkyl), aryl, vinyl and heteroaryl. Examples of $R^1$ include methyl, ethyl, propyl, butyl, pentyl, hexyl, heptyl, octyl, nonyl, decyl, dodecyl, tridecyl, tetradecyl, pentadecyl, hexadecyl, heptadecyl, and octadecyl. Preferably, R1 contains 1 to 22 carbon atoms, more preferably 1 to 10 carbon atoms, including 2, 3, 4, 5, 6, 7, 8 and 9 carbon atoms. An example of an organo oxysilane moiety is octylsilane.

The second alkoxy silane is selected from the group consisting of a poly(dialkyl)siloxane, and mixtures thereof. Poly(dialkyl)siloxanes are preferably oligomers of the formula $R^cO(SiR^2{}_2)(R^2{}_2SiO)_n(SiR^2{}_2)OR^c$, where n is an integer of 2 to 14, preferably 4 to 10, including 5, 6, 7, 8 and 9. Each $R^2$ is an organic group such as methyl, ethyl, or phenyl, and each $R^c$ is an end blocking group such as alkyl including methyl, ethyl, and propyl to form an alkyloxy group, or H to form a hydroxyl group; hydroxy and alkyloxy groups are both reactive groups. It is also possible that 1 to 3 of the $R^2$ groups are hydroxyl and/or alkyloxy groups. $R^2$ and $R^c$ each independently preferably contain 1 to 22 carbon atoms, more preferably 1 to 10 carbon atoms, including 2, 3, 4, 5, 6, 7, 8 and 9 carbon atoms. Preferably, the poly(dialkyl)siloxane is a polydimethylsiloxane or a polydiethylsiloxane. Preferably, the poly(dialkyl)siloxanes have a weight average molecular weight of 200 to 10,000, more preferably 500 to 5,000.

The second alkoxy silane the may contain poly(dialkyl)siloxane moieties. Poly(dialkyl)siloxane moieties are $O(SiR^2{}_2)(R^2{}_2SiO)_n(SiR^2{}_2)O$ or $O(SiR^2{}_2)(R^2{}_2SiO)_n(SiR^2{}_2)OR^c$ groups which bond to other atoms, where n is an integer of 2 to 14, preferably 4 to 10, including 5, 6, 7, 8, and 9. Each $R^2$ is independently an organic group such as methyl, ethyl, or phenyl, and each $R^c$ is an end blocking groups such as alkyl including methyl, ethyl, and propyl to form an alkyloxy group, or H to form a hydroxyl group; hydroxy and alkyloxy groups are both reactive groups. It is also possible that 1 to 3 of the $R^2$ groups are hydroxyl and/or alkyloxy groups. $R^2$ and $R^c$ each independently preferably contain 1 to 22 carbon atoms, more preferably 1 to 10 carbon atoms, including 2, 3, 4, 5, 6, 7, 8, and 9 carbon atoms. Preferably, the poly(dialkyl)siloxane moiety is a polydimethylsiloxane moiety or a polydiethylsiloxane moiety.

Typically, the particles and the three components of the composition are thoroughly mixed together, and then placed into a sealed vessel. The vessel is then evacuated and heated to a temperature where at least two of components form vapor. The temperature is maintained for sufficient time to allow polymerization and formation of a coating on the particles, preferably with continuous mixing during the polymerization process. Carrying out the polymerization reaction for a longer duration allows for a more complete coating of the particle surface. The vessel is then flooded with an inert gas stream which allows the removal of volatile by-products such as alcohols and is subsequently allowed to cool to room temperature. The polymer coating formed contains moieties of each of the three silanes: (1) silica moieties, (2) organo oxysilane moieties selected from the group consisting of mono-organo oxysilane moieties, bi-organo oxysilane moieties and tri-organo oxysilane moieties, and (3) poly(dialkyl)siloxane moieties.

Preferably, the temperature of polymerization is 80° C. to 120° C., more preferably 90° C. to 110° C., including 92, 94, 96, 98, 100, 102, 104, 106, and 108° C. Preferably the amount of time for polymerization is 0.5 to 10 hours, more preferably 1 to 6 hours, including 2, 3, 4, and 5 hours.

After the polymerization process, the coated powder is heated to 120° C. in order to evaporate any volatile compounds. This drying removes very little weight. For purposes of determining the amount of $SiO_2$ equivalents of silicon in the coating, the coated powder is heated to a temperature from 600° C. to 800° C. This process can be carried out in a thermogravimetric device or other devices. Combustion to either 600° C. or 800° C. in air will convert all the silicon containing moieties in the coated powder to $SiO_2$. The composition of the ignited powder can be confirmed by a variety of assay methods.

A variety of techniques are available to analyze the coated powder of the present invention. The inorganic oxide particles may be dissolved with various acids, determining the relative amount of polymer and inorganic oxide, and then the remaining polymer coating may be examined using FTIR (Fourier Transform Infrared Spectroscopy) to determine the presence of different moieties and the relative amounts of each moiety. Other techniques, such as mass spectrometry, TGA (Thermogravimetric Analysis), or ICP (Inductively Coupled Plasma Spectroscopy) may also be used to establish relative monomer unit ratios. A baseline may be established by using a standard of known composition.

The coated powder may also be analyzed by solid state NMR, examining $^{13}C$ and $^{29}Si$ NMR signals to determine the presence of different moieties and the relative amounts of each moiety. Furthermore, the inorganic oxide particles may be dissolved with various acids, and the remaining polymer coating may be analyzed by NMR, examining $^{13}C$ and $^{29}Si$ NMR signals to determine the presence of different moieties and the relative amounts of each moiety. A baseline may be established by using a standard of known composition.

The coated powders may be examined for properties using the photostability test, the chemical reactivity test and the hydrophobicity test. The coated powders are super-photostable, under the $TiO_2$ photostability test, if the coated powders have a photostability of $\Delta E \leq 15$, preferably $\Delta E = 1$ to 14, including $\Delta E = 2, 3, 4, 5, 6, 7, 8, 9, 10, 11, 12$ and $13$. The coated powders are super-photostable, under the DPPH photostability test, if the coated powders have a photostability of $\Delta E \leq 4.5$, preferably $\Delta E = 1$ to 4, including $\Delta E = 4.0, 3.5, 3.0, 2.5, 2.0, 1.5$ and $1.0$. The coated powders are super-photostable, under the effects pigments photostability test, if the coated powders have a photostability of $\Delta E \leq 1.15$, preferably $\Delta E = 0.5$ to $1.0$, including $1.05, 0.95, 0.85, 0.75, 0.65$ and $0.55$. Preferably, the coated powders have a chemical reactivity of $\Delta E = 0$ to $20$, more preferably $\Delta E = 0$ to $17$, most preferably $\Delta E = 0, 1, 2, 3, 4, 5, 6, 7, 8, 9, 10, 11, 12, 13, 14, 15$, or $16$. Preferably the coated powders are hydrophobic or marginally hydrophobic, most preferably hydrophobic.

The coated powder may be used to form dispersions with non-polar liquids, preferably cosmetic oils, such as capric/caprylic triglycerides, linear alkyl benzoate, ethylhexyl benzoate, natural product oils, and silicone oils. Preferably, the dispersions contain at least 40% by weight coated powder (solids), more preferably at least 50% by weight coated powder (solids), including at least 55% by weight coated powder (solids), at least 60% by weight coated powder (solids), and at least 65% by weight coated powder (solids), such as 50-65% by weight coated powder (solids), and 55-60% by weight coated powder (solids). Such dispersions may be made by a variety of conventional mixing processes, including mixing with a rotor-stator machine, planetary mixing, high-pressure homogenizers, ultra-sonic mixing, and media milling. An adjunct emulsifier or dispersant may be included in the dispersions. Examples include tricereareth-4 phosphate (Hostaphat KW 340 D; Clariant) at 5-15% by weight of solids.

Surprisingly, high solids dispersions of the coated powders have relatively low viscosity. Preferably, the viscosity is at most 60,000 cP, more preferably at most 30,000 cP, most preferably at most 6,000 cP. Examples include a viscosity of 1,000 to 50,000 cP, and 5,000 to 30,000 cP.

One preferred aspect of the present invention includes the addition of antioxidants to dispersions containing the coated powders. Antioxidants are oxidized when exposed to UV radiation, leading to a decrease in the antioxidative power. Additionally, zinc oxide and other metal oxides are photoreactive, and produce free radicals upon UV radiation exposure. Metal oxides, in combination with antioxidants, would have a greater loss of AP than the antioxidants alone. However, by combining coated powders with antioxidants, the relative AP value of the dispersion remains higher than that of the antioxidants alone. Because the coated powders are super-photostable, compositions of coated powders and antioxidants exhibit a synergistic effect together. The antioxidants are able to be effective, because UV radiation is blocked or absorbed by the particles, preserving the AP value.

Dispersions may contain one or more antioxidant. Antioxidants may include vitamins, antioxidant minerals, antioxidant proteins, antioxidant enzymes and coenzymes, phytonutrients, antioxidant hormones, mycosporine-like amino acids (MAAs), antioxidants derived from marine algae, and other types of antioxidants. Antioxidants may be water soluble, fat soluble, or fat and water soluble. Suitable vitamins include vitamin A (including retinoids and carotenoids), vitamin C (ascorbic acid), vitamin E (tocopherols), and vitamin K. Suitable retinoids include retinol, retinoic acid (tretinoin), retinal and retinyl palmitate. Suitable minerals include copper, manganese, iodide and zinc. Suitable enzymes and coenzymes include melatonin, superoxide dismutase, catalase, and glutathione peroxidase. Suitable phytonutrients include carotenoids, flavonoids, phenolic acids, and nonflavonoid phenolics. Suitable carotenoids include alpha-carotene, retinol, astaxanthin, beta-carotene, canthaxanthin, lutein, lycopene, and zeaxanthin. Suitable flavonoids include hindered phenols, apigenin, luteolin, tangeritin, isohamnetin, kaempferol, myricetin, proanthocyanidins, quercetin, eriodictyol, hesperetin, naringenin, catechin, gallocatechin, epicatechin, epigallocatechin, thearubigins, daidzein, genistein, glycitein, resveratrol, pterostilbene, cyanidin, delphinidin, malvidin, pelargonidin, and petunidin. Suitable phenolic acids include phenol, polyphenols, alkylated phenols, and hindered phenols. Suitable phenols include butylated hydroxyanisole, butylated hydroxytluene, cannabinoids, capsaicin, carvacrol, cresol, estradiol, eugenol, gallic acid, guaiacol, thymol, tyrosine, and sesamol. Gallic acid includes salts and esters of gallic acid, also known as gallates. Suitable nonflavonoid phenolics include curcumin, flavonolignans, xanthones, and eugenol. Suitable mycosporine-like amino acids (MAAs) include mono-substituted MAAs, such as mycosporine-gycine and mycosporine-taurine, di-substituted MAAs, such as palythenic acid and shinorine, and derivatized MAAs, such as palythine-threonine sulfate and palythine-threonine glycoside. Examples of suitable MAAs can be found in Wada et al. (2015). Antioxidants derived from marine algae include ascorbate, glutathione, phlorotannins, eckol, eckstolonol, prenyl toluquinones, tetraprenyltoluquinols, sargothunbergol A, fucodiphlorethol, terpenoids, phycocyanin, phycocyanobilin, fucoxanthin, phlorotannin, and lutein. Other potential organic antioxidants include bilirubin, citric acid, oxalic acid, phytic acid, n-acetylcysteine, uric acid, green tea, hydoxy-tryrosol, dihydo-quercetin, ubiquinone, glutathione, alpha-lipoic acid, folic acid, ellagic acid, caffeic acid, and phytoestrogens. The antioxidants above also include any salt, ester or acid form of the antioxidant.

Dispersions may contain one or more phyto-extracts. A "phyto-extract" is a substance obtained from a plant. Preferably, the phyto-extract imparts a color. Phyto-extracts must be compatible with non-aqueous compositions; stable in air; non-staining to skin; non-irritating to skin in the amount used; and non-toxic in the amounts used. The phyto-extract has a purity level of at least 95%. Examples of suitable phyto-extracts include curcumin, lycopene, beta-carotene, lutein, zeaxanthin, meso-zeaxanthin and anthocyanins. Sources of curcumin include turmeric. Sources of lycopene include beets, cherries, goji berries, pink grapefruit, pomegranate, raspberries, red cabbage, red onions, strawberries, tomatoes and watermelon. Sources of beta-carotene include apricots, cantaloupes, carrots, oranges, papayas, peaches, persimmons, pumpkins, summer squash, sweet potatoes, winter squash and yams. Sources of lutein, zeaxanthin, and meso-zeaxanthin include avocados, broccoli, Brussels sprouts, cabbage, green beans, leafy greens, orange peppers, peas, spinach, yellow corn and zucchini. Sources of anthocyanins include beets, black currants, blueberries, cherries, eggplant, figs, grapes, plums, prunes, red cabbage and red currants. Phyto-extracts may be chemically modified by hydrolysis, hydrogenation, esterification or saponification. Phyto-extracts which normally impart a color may no longer impart a color if they have been chemically modified. For example, curcumin imparts a yellow color but tetra-hydro curcumin, which has been hydrogenated, is colorless.

Dispersions may contain one or more plant bio-extracts. A "plant bio-extract" is a natural extract of a plant that provides a fragrance and may also provide a color. Plant bio-extracts must be compatible with non-aqueous compositions; stable in air; non-staining to skin; non-irritating to skin in the amounts used; and non-toxic in the amounts used. Synthetic versions of plant bio-extracts are outside the scope of the term "plant bio-extract." Examples of suitable plant bio-extracts include arnica extract (*Arnica montana*), basil extract (*Ocimum basilicum*), boswellia extract (*Boswellia sacra*), calendula extract (*Calendula officinalis*), chamomile extract (*Anthemis nobilis*), cinnamon oil (*Cinnamomum verum*), clove oil (*Syzygium aromaticum*), coptis extract (*Coptis aspleniifolia*), echinacea extract (*Echinacea purpurea*), eucalyptus oil (*Eucalyptus occidentalis*), ginger root extract (*Zingiber officinale*), grape seed extract (*Vitis vinefera*), green tea extract (*Camilia sinensis*), guggul resin extract (*Commiphora wightii*), horse chestnut seed extract (*Aesculus hippocastanum*), Japanese knotweed extract (*Polygonum cuspidatum*), licorice extract (*Glycyrrhiza glabra*), neem leaf extract (*Azadirachta indica*), olive fruit and olive leaf extract (*Olea europaea*), papaya extract (*Carica papaya*), Peruvian balsam (*Myroxylon balsamum*), pineapple extract (*Ananas comosus*), pomegranate extract (*Punica granatum* L.), rosemary extract (*Rosmarinus officinalis*), sage extract (*Salvia officinalis*), sandalwood extract (*Santalum album*), turmeric extract (*Curcuma longa*) and witch hazel extract (*Hamamelis japonica*). All the above examples may include different species of the same genus of plant. For example, witch hazel extract may be obtained from *Hamamelis japonica, Hamamelis ovalis, Hamamelis mollis* or *Hamamelis virginiana*.

The composition optionally includes a phyto-extract. The phyto-extract may be selected to provide a color. Phyto-extracts that do not impart a color may also be included in the composition. Phyto-extracts must be compatible with non-aqueous compositions; stable in air; non-staining to skin; non-irritating to skin in the amounts used; and non-toxic in the amounts used. The phyto-extract has a purity level of at least 95%. Examples of suitable phyto-extracts include curcumin, lycopene, beta-carotene, lutein, zeaxanthin, meso-zeaxanthin and anthocyanins. Sources of curcumin include turmeric. Sources of lycopene include beets, cherries, goji berries, pink grapefruit, pomegranate, raspberries, red cabbage, red onions, strawberries, tomatoes and watermelon. Sources of beta-carotene include apricots, cantaloupes, carrots, oranges, papayas, peaches, persimmons, pumpkins, summer squash, sweet potatoes, winter squash and yams. Sources of lutein, zeaxanthin, and meso-zeaxanthin include avocados, broccoli, Brussels sprouts, cabbage, green beans, leafy greens, orange peppers, peas, spinach, yellow corn and zucchini. Sources of anthocyanins include beets, black currants, blueberries, cherries, eggplant, figs, grapes, plums, prunes, red cabbage and red currants. Phyto-extracts may be chemically modified by hydrolysis, hydrogenation, esterification or saponification. Phyto-extracts which normally impart a color, such as curcumin, may no longer impart a color if they have been chemically modified, such as tetra-hydro curcumin. The composition may contain 0.01% to 5.0% phyto-extract, preferably 0.01% to 1.0% phyto-extract, including 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19% and 0.20% phyto-extract.

The composition optionally includes a plant bio-extract. The plant bio-extract provides a fragrance and may also provide a color. Plant bio-extracts must be compatible with non-aqueous compositions, such as being lipophilic or hydrophobic; stable in air; non-staining to skin; non-irritating to skin in the amounts used; and non-toxic in the amounts used. Examples of suitable plant bio-extracts include arnica extract (*Arnica montana*), basil extract (*Ocimum basilicum*), boswellia extract (*Boswellia sacra*), calendula extract (*Calendula officinalis*), chamomile extract (*Anthemis nobilis*), cinnamon oil (*Cinnamomum verum*), clove oil (*Syzygium aromaticum*), coptis extract (*Coptis asplenii-*

*folia*), echinacea extract (*Echinacea purpurea*), eucalyptus oil (*Eucalyptus occidentalis*), ginger root extract (*Zingiber officinale*), grape seed extract (*Vitis vinefera*), green tea extract (*Camilla sinensis*), guggul resin extract (*Commiphora wightii*), horse chestnut seed extract (*Aesculus hippocastanum*), Japanese knotweed extract (*Polygonum cuspidatum*), licorice extract (*Glycyrrhiza glabra*), neem leaf extract (*Azadirachta indica*), olive fruit and olive leaf extract (*Olea europaea*), papaya extract (*Carica papaya*), Peruvian balsam (*Myroxylon balsamum*), pineapple extract (*Ananas comosus*), pomegranate extract (*Punica granatum* L.), rosemary extract (*Rosmarinus officinalis*), sage extract (*Salvia officinalis*), sandalwood extract (*Santalum album*), turmeric extract (*Curcuma longa*) and witch hazel extract (*Hamamelis japonica*). The dispersion may optionally include extracts from algae species. These species include *Hijikia fusiformis, Spirulina platensis, Aphanizomenon, Spirulina maxima, Sargassum kjellamanianum, S. siliquastrum, Rhodomela confervoides, Symphjocladia latiuscula, Kappaphycus alvarezzi, Botryococcus braunii, Dunaliella salina, Cystoseira crinite, Ecklonia stolonifera, Sargassum thunbergii, S. thunbergii,* and *Ecklonia cava*. The composition may contain 0.10% to 10.0% plant bio-extract, preferably 2.0% to 6.0% plant bio-extract, including 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9% and 4.0% plant bio-extract.

The composition optionally includes an oil-soluble antioxidant. When an antioxidant is present, the antioxidant is different than the phyto-extract. Examples of suitable antioxidants include carotene, catechin, lycopene, resveratrol, Vitamin E or Vitamin A. "Vitamin E" may refer to any of the tocopherol or tocotrienol compounds that constitute the Vitamin E family of compounds, such as alpha-tocopherol and gamma-tocotrienol. The composition may contain 0.01% to 5.0% antioxidant, preferably 0.1% to 3.0% antioxidant, including 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0% antioxidant.

The dispersion may contain one or more protist extract. A "protist extract" is a substance obtained from a protist. Protists include eukaryotic organisms that are not animals, plants or fungi. Preferably the protist extract is a substance that is high in astaxanthins. Examples of suitable protist extracts include plankton extract and algae extract, particularly red algae extract.

The dispersion may optionally include a protist extract. Preferably the protist extract is a substance that is high in astaxanthins. Examples of suitable protist extracts include plankton extract and algae extract, particularly red algae extract. The dispersion may contain 0.01% to 5.0% protist extract, preferably 0.1% to 3.0% protist extract, including 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0% protist extract. Cosmetic and dermatological preparations may include cosmetic ingredients, auxiliaries and/or additives, for example, co-emulsifiers, fats and waxes, stabilizers, thickeners, biogenic active ingredients, film formers, fragrances, dyes, pearlizing agents, preservatives, pigments, electrolytes, and pH regulators. Suitable co-emulsifiers are, preferably, known W/O and also O/W emulsifiers, for example, polyglycerol esters, sorbitan esters or partially esterified glycerides. Typical examples of fats are glycerides; waxes such as beeswax, paraffin wax or microcrystalline waxes, optionally in combination with hydrophilic waxes. Stabilizers including metal salts of fatty acids, for example, magnesium, aluminum and/or zinc stearate. Examples of thickeners include crosslinked polyacrylic acids and derivatives thereof, polysaccharides, such as xanthan gum, guar gum, agar, alginates and tyloses, carboxymethylcellulose and hydroxyethylcellulose, and fatty alcohols, monoglycerides and fatty acids, polyacrylates, polyvinyl alcohol and polyvinylpyrrolidone. Biogenic active ingredients include plant extracts, protein hydrolyzates and vitamin complexes. Customary film formers include, for example, hydrocolloids, such as chitosan, microcrystalline chitosan or quaternary chitosan, polyvinylpyrrolidone, vinylpyrrolidone/vinyl acetate copolymers, polymers of the acrylic acid series, and quaternary cellulose derivatives. Examples of preservatives include parabens, diazolidinyl urea, iodopropynyl butylcarbamate, and sorbic acid. Examples of pearlizing agents include glycol distearic esters, such as ethylene glycol distearate, fatty acids and fatty acid monoglycol esters. Dyes which may be used are the substances suitable and approved for cosmetic purposes. Antioxidants, such as amino acids, retinol, flavonoids, polyphenols, vitamin C and tocopherols, may also be included.

The cosmetic and dermatological preparations may be in the form of a solution, dispersion or emulsions; for example, sunscreen preparations may be in liquid, paste or solid form, for example as water-in-oil creams, oil-in-water creams and lotions, aerosol foam creams, gels, oils, marking pencils, powders, sprays or alcohol-aqueous lotions. Solvents for these compositions include water; oils, such as triglycerides of capric acid or of caprylic acid, as well as castor oil; fats, waxes and other natural and synthetic fatty substances, esters of fatty acids with alcohols of low carbon number, for example with isopropanol, propylene glycol or glycerol, or esters of fatty alcohols with alkanoic acids of low carbon number or with fatty acids; alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether. Other examples include isopropyl myristate, isopropyl palmitate, isopropyl stearate, isopropyl oleate, n-butyl stearate, diisopropyl adipate, n-hexyl laurate, n-decyl oleate, glyceryl stearate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and erucyl erucate.

The cosmetic and dermatological preparations may be in the form of solid sticks, and may include natural or synthetic waxes, fatty alcohols or fatty acid esters, liquid oils for example paraffin oils, castor oil, isopropyl myristate, semi-solid constituents for example petroleum jelly, lanolin, solid constituents such as beeswax, ceresine and microcrystalline waxes and ozocerite, and high-melting waxes including carnauba wax and candelilla wax.

Cosmetic preparations may be in the form of gels and preferably include water, organic thickeners, for example gum arabic, xanthan gum, sodium alginate, cellulose derivatives such as methylcellulose, hydroxymethylcellulose, hydroxyethylcellulose, hydroxypropylcellulose, hydroxypropylmethylcellulose and inorganic thickeners, such as aluminum silicates, for example, bentonites, or a mixture of polyethylene glycol and polyethylene glycol stearate or distearate.

The coated powders and dispersions may also be included in paints, sealants and other coatings, which may also contain binders such as polyacrylates, polyurethanes, polyalkyds, polyepoxides, polysiloxanes, polyacrylonitriles and/or polyesters. Organic solvents may also be present, including ethanol, butyl acetate, ethyl acetate, acetone, butanol, alkanes, methanol, propanol, and pentanol; ethers/acetals such as tetrahydrofuran and 1,4-dioxane; ketones such as diacetone alcohol, and methyl ethyl ketone; and polyhydric alcohol derivatives such as ethylene glycol, propylene glycol, and diethylene glycol or mixtures thereof. These compositions may be used to coat a variety of substrates, including wood, PVC (polyvinyl chloride), plastic, steel, aluminum, zinc, copper, MDF (medium density fiberboard), glass and concrete. Depending on which coated powders are included, the compositions provide the substrate with a coating that may be transparent, UV-resistant, and/or provide greater scratch resistance.

The coated powder and dispersions may be blended with a resin, to provide an organic polymer composite. Examples of resins include, polyethylene, polypropylene, polystyrene, polyethylene terephthalate, AS (acrylonitrile styrene) resins, ABS (acrylonitrile butadiene styrene) resins, AES (acrylonitrile ethylene styrene) resins, polyvinylidene chloride, methacrylic resins, polyvinyl chloride, polyamides, polycarbonates, polyallyl esters, polyimides, polyacetals, polyether ketones, polyether sulfones, polyphenyl oxides and polyphenylene sulfides, as well as mixtures thereof. Also present in these compositions may be coloring agents, fluorescent agents, and additives, such as antioxidants, anti-aging agents, UV-absorbers, lubricants, antistatic agents, surfactants, fillers (the coated powder and dispersions may also act as fillers), plasticizers, stabilizers, blowing agents, expanding agents, electroconductive powder, electroconductive short fiber, deodorizing agents, softening agents, thickeners, viscosity-reducing agents, diluents, water-repellent agents, oil-repellent agents, cross-linking agents and curing agents. These organic polymer compositions may be shaped by a variety of techniques, including injection molding, blow molding, extrusion molding, calender molding, flow molding, compression molding, melt-blown molding, and the spun bond method, whereby shape-imparted products such as fiber, thread, film, sheets, tapes, and injection-molded products and shaped bodies such as hollow thread, pipes, and bottles may be produced. Alternatively, the compositions can be subjected to secondary molding methods generally applied to thermoplastic resins such as vacuum forming, air pressure forming, and laminate molding.

EXAMPLES

The $TiO_2$, DPPH and effects pigments photostability tests are customized tests. The different colorimeter photostability tests are designed to provide a high level of sensitivity for the various materials. Each material has different absorption bands and reactivity, so different tests are needed to accurately measure the resultant color change upon UV radiation exposure. For example, $TiO_2$ is typically not tested using DPPH because the $TiO_2$ is very reactive with the DPPH. The three colorimeter tests are able to performed quickly and easily by comparing the color change in a sample to a standard. The testing results can be validated by using other testing methods such as Electron Spin Resonance (ESR) spectroscopy.

Example 1

The improved photostability of the coated powder can be measured using the $TiO_2$ photostability test described above. In this test, a pass condition is $\Delta E \leq 15$ based on experience with spectrophotometric tests which include selected antioxidants and the ESR-based methods. The data in Table 1 below were based on a constant 40 $m^2/g$ (35 nm) rutile phase $TiO_2$ particle. Since the coating surface coverage is based on surface areas, the mass fractions of the coating components should be scaled to the specific surface areas of the base particles. Modeling the responses suggests that the pass/fail condition is traversed when A+B exceeds 2.5% for the case below. Since the common base particle is 40 $m^2/g$ in this case, the pass/fail boundary is expressed as 0.0625% per $m^2/g$ for all particle types. As shown in Table 1 below, all compositions that meet the criteria have a $\Delta E \leq 15$.

TABLE 1

Photostability Test Results

|  | $TiO_2$ | $SiO_2$ from Propylsilane Moieties (A) | $SiO_2$ from Silicate Moieties (B) | $SiO_2$ from Polydimethylsiloxane Moieties | $\Delta E$ Resorcinol Test | A + B | Pass/Fail |
| --- | --- | --- | --- | --- | --- | --- | --- |
| (i) | 92.7% | 4.7% | 0.149% | 2.5% | 14.4 | 4.9% | Pass |
| (ii) | 92.2% | 2.0% | 0.148% | 5.7% | 16.5 | 2.2% | Fail |
| (iii) | 87.1% | 9.2% | 1.835% | 1.9% | 11.6 | 11.0% | Pass |
| (iv) | 92.9% | 6.1% | 0.150% | 0.8% | 14.5 | 6.2% | Pass |
| (v) | 91.9% | 0.7% | 0.148% | 7.3% | 23.9 | 0.8% | Fail |
| (vi) | 93.0% | 6.1% | 0.075% | 0.8% | 14.5 | 6.2% | Pass |
| (vii) | 92.0% | 0.7% | 0.074% | 7.3% | 21.7 | 0.7% | Fail |
| (viii) | 92.8% | 4.7% | 0.075% | 2.4% | 14.2 | 4.8% | Pass |
| (ix) | 92.2% | 2.0% | 0.074% | 5.7% | 16.3 | 2.1% | Fail |

The coating components are expressed in terms of weight % of each moiety of total powder (inorganic substrate plus coating) as opposed to the reactant amounts, since the coatings only consist of cross-linked polymers of the residues. Not all of the component material will react with the particle surface, so it is more accurate to measure the weight percent of $SiO_2$ present from each moiety in the coating after ignition.

Example 2

W/O formulations containing physical UV-filters (150 nm zinc oxide) were analyzed regarding the amount of UV-inducible free radicals using the radical potential (RP) method below.

A semistable spin probe PCA (2,2,5,5-tetramethyl pyrrolidine N-oxyl) is added to the test product, the samples are inserted in capillary quartz tubes, and the concentration of the spin marker is monitored by ESR spectroscopy before and after defined UV radiation doses. The PCA spin probe is photostable and resistant to antioxidants, but it promptly reacts with the UV generated free radicals inside the samples (mainly lipid peroxides and lipidic radicals). The amount of UV generated free radicals can be quantitatively detected from a calibration curve.

Materials and Methods

A water/EtOH solution of the spin trap (PCA) was added to the W/O emulsions to obtain a final concentration of 0.01 mM PCA. The samples are inserted into ESR capillary quartz tubes (40 μL), before the ESR measurements and UV irradiation start.

The UV irradiation of the samples was performed with a UV solar simulator 300 W Oriel (Newport). The irradiances as integrated value over the spectral ranges were E (UVB=280–320)=23.5 W/m$^2$ and E (UVA=320–400nm)= 180 W/m$^2$. To test the effect of different UV doses the irradiation time was varied. The emitting intensity is controlled before each measurement. The measurements were performed with a commercial high sensitive X-band bench top Electron Spin Resonance Spectrometer MiniScope MS300, (Magnettech GmbH, Berlin, Germany).

Results and Discussion

The amount of UV-induced free radicals inside cosmetic formulations was measured. Knowing the concentration of the spin trap PCA within the sample (0.01 mM), the amount of reduced PCA can be calculated. Since one electron is needed to reduce 1 molecule of PCA, the radical concentration inside the sample can be calculated using a calibration curve. The percent of induced free radicals corresponding to each product is shown in Table 2.

TABLE 2

Relative and Absolute Amounts of Free Radicals

| Product | % of induced free radicals | induced free radicals (μM) | ±sd |
|---|---|---|---|
| placebo (comparative) | 8.6 | 0.857 | 0.79 |
| ZnO (comparative) | 24.6 | 2.462 | 0.28 |
| ZnO + Octyltriethoxysilane coating (comparative) | 27.4 | 2.743 | 0.06 |
| ZnO + Multifunctional coating | 2.8 | 0.284 | 0.27 |

Figure 1:
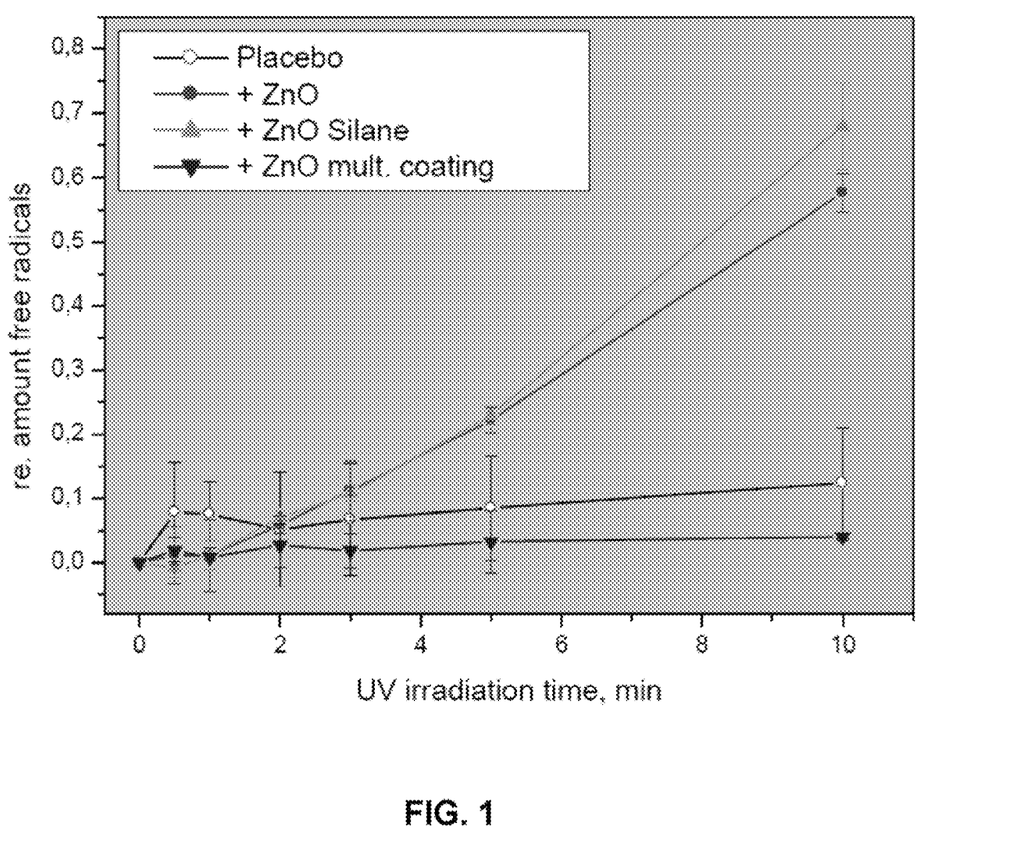
FIG. 1 is a graph of the relative percentage of free radicals as the UV irradiation time changes.

Two different coating technologies for ZnO coating were tested. With respect to the uncoated material, no protective effect was seen in the sample having a coating formed from octyltriethoxysilane. On the contrary, radical formation was reduced to less than 3% in the sample containing ZnO with a multifunctional coating. The change in the percentage of induced free radicals for the different products as the UV irradiation time changes is shown in FIG. 1. The materials and monomers used to form the multifunctional coating components are shown in Table 3, below.

TABLE 3

Components of Multifunctional coating

| Component | % by Weight |
|---|---|
| Propylsilane moieties | 5.5% |
| Silicate moieties (from tetrafunctional silane) | 0.8% |
| Polydimethyl siloxane moieties | 0.9% |
| 150 nm ZnO | 92.8% |

Example 3

In the presented test design, different photo-unstable antioxidants have been added to formulations containing ZnO with different coating technologies. The antioxidative activity of these formulations was determined, using the AP method, before and after UV irradiation of the formulations.

The antioxidants have been chosen according to the following criteria: (1) The antioxidants used are suitable to be used in cosmetic formulations, and (2) The 5 raw materials represent different classes of antioxidants having different molecular mechanism, hydrophilic and lipophilic character. The final concentrations of each antioxidants were chosen based on the antioxidative capacity of the raw materials. All concentrations stayed within the range of recommended use, based on EU-guidelines.

Antioxidants are oxidized when exposed to UV radiation, leading to a decrease in the antioxidative power (AP). Table 4 below, shows that the AP decreases upon exposure to UV radiation. The "after UV" column information was collected after 10 minutes of UV radiation exposure, which is equivalent to 2.4 MEDs (minimal erythermal doses). While antioxidants would reduce the number of free radicals, exposure to UV radiation greatly reduces the AP of antioxidants.

TABLE 4

Loss of AP with UV Radiation Exposure.
In the placebo

| | Before UV | After UV |
|---|---|---|
| | AP (%) | AP (%) |
| Ascorbic acid 0.05% | 100 | 8 |
| Tocopherol 0.5% | 100 | 0 |
| Green tea 0.05% | 100 | 2 |
| Hydroxytyrosol 0.05% | 100 | 42 |
| Quercetin 0.1% | 100 | 74 |

Materials and Methods

The measurements of the antioxidant capacity and reactivity were performed by using ESR spectroscopy. Since this spectroscopic technique is able to quantify free radicals and since it is applicable to opaque, viscous, and colored samples, it is particular suitable for the analysis of antioxidants in cosmetic products. The measurements were performed with the X-band ESR spectrometer Miniscope MS 300 (Magnettech, Germany) and the following technical parameters: 60 G sweep width, 100 Gain, 1 G modulation amplitude, 7 mW attenuation, 3365 G central field, 0.14 sec time constant. The Antioxidative Power (AP) is a parameter able to quantify both the reaction capacity and velocity of antioxidants. The test radical DPPH (2,2-diphenyl-1-picrylhydrazyl, Sigma-Aldrich, Munich, Germany) is used as a detector molecule. At least 3 concentrations of the test sample were prepared and added to DPPH to obtain an initial radical concentration of 0.1 mM. The signal intensity decay of each concentration of the test samples is recorded at different time intervals during the reaction until saturation is reached and all antioxidant active molecules have reacted with the test radical.

From these intensities, a first order kinetic was obtained for each concentration set. The kinetic parameters are used to calculate the reaction time ($t_r$) and the static parameters are used to calculate the characteristic weight ($w_c$).

For a direct comparison of different antioxidants, the AP method is standardized to the activity of vitamin C (ascorbic acid, supplied by Sigma-Aldrich, Munich, Germany, at the highest grade of purity). The antioxidative activity of a solution of 1 ppm vitamin C is defined as an antioxidative unit (AU). For each formulation, the AP value before and after exposure to UV radiation was determined.

Results 300 mg of each formulation was applied on a glass plate (microscope slide) and exposed to UV radiation using a sun simulator (Hönle SOL 2 sun simulator) for 10 minutes (22.7 J/cm$^2$). The products are collected from the slides and the AP is determined. The weight of the samples before and after UV exposure was controlled for each sample. The weight loss due to water evaporation was below 5% for all of the samples.

The formulations containing ZnO, independently from the coating, showed a protective effect during the relatively low UV irradiation. Therefore, the products containing 10% of ZnO were diluted by a factor 4 using the placebo. The following experiments were therefore conducted with formulations containing 2.5% of ZnO. The formulations containing 2.5% ZnO showed photoprotective effects for most of the antioxidants used, due to the UV-scattering effect.

Nevertheless, there is a significant difference between the two ZnO preparations: The antioxidants were less stable in the formulations containing ZnO having a coating formed from octyltriethoxysilane, compared to the ZnO having a multifunctional coating.

Figure 2:
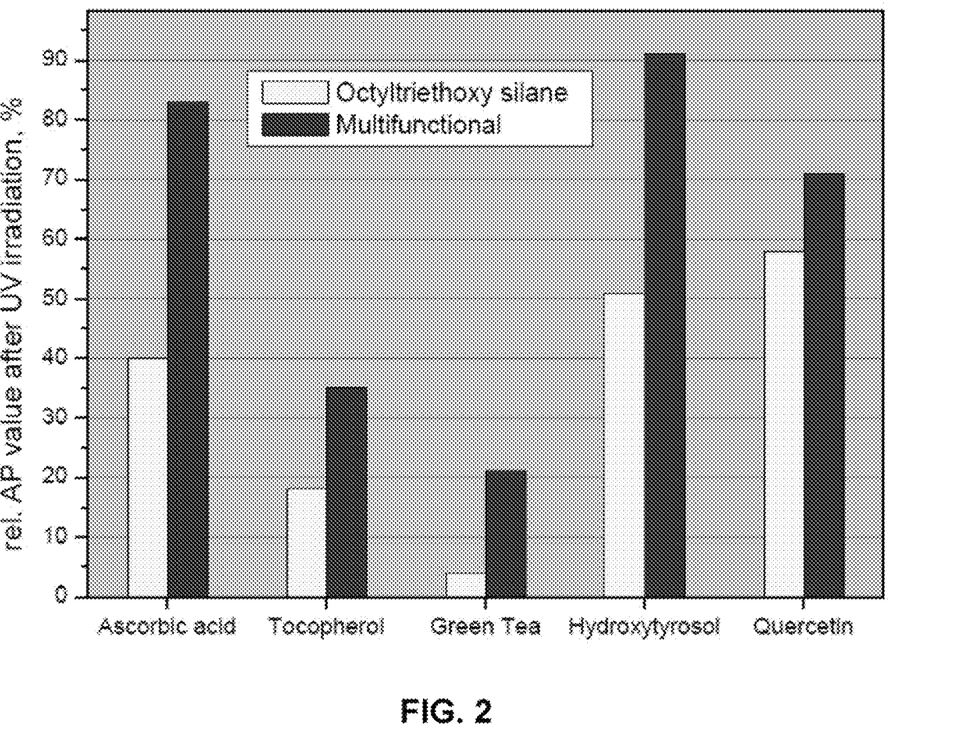
FIG. 2 is a graph of the relative AP value after UV irradiation for various antioxidants, when in combination with either ZnO having an octyltriethyloxy silane coating or ZnO having a multifunctional coating.

The generation of UV-inducible free radicals was evaluated for the two ZnO-containing formulas (see Example 2 above). The particles having the multifunctional coating showed no radical generation, whereas in the formula containing ZnO having a coating formed from octyltriethoxy silane, a high photo-catalytic activity was observed. This photocatalytic activity will lead to the generation of hydroperoxides, mainly hydroxyl radicals, which promptly react with the antioxidants, leading to an oxidation and a consequent decrease in their AP. FIG. 2 shows the relative AP values after UV irradiation are greater for the multifunctional coating than for the coating formed from octyltriethoxy silane. Data showing that the relative AP values after UV irradiation are greater for the multifunctional coating than for the coating formed from octyltriethoxy silane can be seen in Table 5.

TABLE 5

Antioxidative Power Before and After UV Irradiation.

| | Before UV | | | After UV | | |
|---|---|---|---|---|---|---|
| | AP (AU) | $t_r$ (min) | $w_c$ (mg) | AP (AU) | $t_r$ (min) | $w_c$ (mg) |
| Ascorbic acid 0.05% in: | | | | | | |
| Placebo | 550 | 0.24 | 2.51 | 45 | 0.24 | 30.99 |
| ZnO Octyltriethoxysilane | 338 | 0.24 | 4.08 | 136 | 0.24 | 10.15 |
| ZnO Multifunctional | 348 | 0.24 | 3.96 | 288 | 0.24 | 6.31 |
| Tocopherol 0.5% in: | | | | | | |
| Placebo | 103 | 0.30 | 12.09 | 0 | — | — |
| ZnO Octyltriethoxysilane | 123 | 0.30 | 8.99 | 22 | 0.48 | 31.94 |
| ZnO Multifunctional | 270 | 0.30 | 3.74 | 94 | 0.30 | 19.47 |
| Green tea 0.05% in: | | | | | | |
| Placebo | 423 | 0.37 | 2.10 | 10 | 0.53 | 28.33 |
| ZnO Octyltriethoxysilane | 419 | 0.37 | 2.13 | 16 | 0.82 | 25.27 |
| ZnO Multifunctional | 252 | 0.37 | 3.55 | 54 | 0.42 | 14.98 |
| Hydroxytyrosol 0.05% in: | | | | | | |
| Placebo | 602 | 0.16 | 3.44 | 255 | 0.22 | 5.888 |
| ZnO Octyltriethoxysilane | 549 | 0.17 | 3.54 | 281 | 0.22 | 5.36 |
| ZnO Multifunctional | 600 | 0.17 | 3.24 | 545 | 0.16 | 4.55 |
| Quercetin 0.1% in: | | | | | | |
| Placebo | 395 | 0.54 | 1.55 | 291 | 0.54 | 2.26 |
| ZnO Octyltriethoxysilane | 378 | 0.54 | 1.62 | 221 | 0.53 | 2.82 |
| ZnO Multifunctional | 396 | 0.54 | 1.55 | 280 | 0.52 | 2.27 |

Example 4

This Example illustrates a coated nanocrystalline TiO$_2$ powder. The coated powder is the coated powder (i) from Table 1. The coated powder, in terms of weight percent, contains 92.7% TiO$_2$, 4.7% SiO$_2$ from propylsilane moieties, 0.149% SiO$_2$ from silicate moieties, and 2.5% SiO$_2$ from polydimethylsiloxane. The ΔE of this sample was 14.4 according to the photostability test. Using an assay, such as X-ray fluorescence (XRF), Inductively Coupled Plasma Spectroscopy (ICP), etc., it is possible to determine the weight percentage of each component of the ignited powder. Using the ratio of the formula weights of the reactants and the formula weight of SiO$_2$, the amount of weight lost during ignition can be calculated.

Example 5

Prophetic

This Example illustrates a coated nanocrystalline ZnO powder. Nanocrystalline ZnO (specific surface area=17 m$^2$/g, corresponding average particle size=63 nm) is coated by propylsilane moieties, silicate moieties, and polydimethylsiloxane moieties. The ZnO particles are coated by the moieties in the same relative proportions as in Example 4. The mixture is homogenized for 30 seconds and then transferred to a glass container which is subsequently sealed. The sealed container is then transferred to an oven where it is heated to a temperature of 100-110° C. and held for 1.5 hours. The resultant coated powder is then dried by unsealing the container and returning the container to the same oven where it is held at a temperature of 100-110° C. for 1.5 hours. The resultant coated powder is highly hydrophobic and is super-photostable. The coated powder of this example and corresponding dispersions are suitable for use in cosmetic sunscreen formulations.

Example 6

Prophetic

This example illustrates a high solids dispersion of the coated powders that is suitable for addition to cosmetic formulations. 460 g of ethylhexyl benzoate (Finsolv® EB; Innospec) and 40 g of an emulsifier are added to a jacketed steel container which is maintained at a constant temperature of 30° C. The emulsifier, tricereareth-4 phosphate (Hostaphat KW 340 D; Clariant) is a waxy solid, anionic O/W emulsifier designed to be used in formulations requiring some level of viscosity such as cream preparations. The contents of the vessel are pre-mixed using a Cowels sawtooth high shear impeller under mild mixing conditions for 5 minutes until the mixture is homogeneous. In the configuration used in this example, the impeller blade diameter is ⅓ of the vessel diameter and is placed 1 blade diameter from the bottom of the vessel. 500 g of the coated $TiO_2$ powder of Example 4 is added to the liquid contents under mild mixing until all the powder is wetted. The mixer speed is then increased to 2500 rpm for 15 minutes. The resultant dispersion is pourable.

Example 7

Prophetic

This Example illustrates a water-in-oil emulsion cosmetic sunscreen preparation containing only inorganic UV screening agents. The following oil-phase ingredients are added to a heated vessel and mixed at low intensity at 80° C. until clear.

TABLE 6

Emulsion Ingredients

| Ingredients | Parts by Weight |
| --- | --- |
| Emulsifier (Abil EM-90: Bis-PEG/PPG Dimethicone, Cyclopentasiloxane; Evonik-Goldschmidt GmbH) | 5.0 |
| 2-Ethylhexyl Palmitate (CAS# 29806-73-3, Crodamol OP; Croda Ltd.) | 11.0 |
| Decamethylcyclopentasiloxane (245 Silicone Oil; Dow Corning) | 7.5 |
| Cetyl Dimethicone (Abil Wax 9801; Evonik-Goldschmidt GmbH) | 3.0 |
| White Mineral Oil (Carnation Oil; Sonneborn) | 2.0 |
| Emollient White Ceresine Wax (Ceresine Sp-252; Strahl & Pitsch) | 1.0 |
| Emollient (Castorwax MP70 Hydrogenated Castor Oil; Vertellus) | 0.5 |

The oil-phase mixture is then cooled to 60° C. and mixed with the coated $TiO_2$ powder of Example 4 (12.0 parts by weight) and subsequently passed through a high shear mixer until the mixture is homogeneous. This mixture is then cooled to 45° C.

The following water-phase ingredients are combined in a separate vessel.

TABLE 7

Water-phase Ingredients

| Ingredients | Parts by Weight |
| --- | --- |
| Deionized water | 56.5 |
| Preservative (Germaben II; ISP) | 1.0 |
| Sodium Chloride | 0.5 |

The homogenized oil-phase mixture and the water phase mixture are mixed until a homogeneous emulsion is formed. Note that optional fragrance (0.2 parts by weight) may be substituted for the equivalent amount of deionized water.

Example 8

Prophetic

This example illustrates a composition comprising the coated powder of Example 5 and an antioxidant, such as hydroxytyrosol. 0.05% hydroxytyrosol is combined with 2.5% ZnO. This composition maintains a greater level of AP because the coated powder blocks UV radiation from oxidizing the antioxidants, while the antioxidants increase the photostability of the composition.

Example 9

Prophetic

This example illustrates a composition comprising the coated powder of Example 4 and tocopherol. This composition maintains a greater level of AP because the coated powder blocks UV radiation from oxidizing the antioxidants, while the antioxidants increase the photostability of the composition.

Example 10

Prophetic

This example illustrates an example of a UV curable coating composition of the present invention. The following ingredients are mixed until homogeneous.

TABLE 8

Ingredients for Composition

| Ingredients | Parts by Weight |
| --- | --- |
| Bisphenol A epoxy acrylate 80% in neopentylglycol propoxylatediacrylate | 44.0 |
| Propoxylated neopentyl glycol diacrylate | 30.9 |
| Ditrimethylolpropane tetraacrylate | 3.2 |
| Benzophenone | 6.0 |
| Acrylated amine synergist (Chivacure OPD; Campbell and Co.) | 9.9 |
| Photoinitiator (Irgacure 184; BASF) | 2.0 |
| Rheology modifier (Bentone 27; Elementis Specialties) | 0.4 |
| Coated ZnO nanopowder of Example 5 | 3.6 |

The composition of this example can be applied as a wet film to a substrate using a wire-wound rod or spray gun and subsequently cured using UV radiation to yield a UV protective hardcoat.

Example 11

This example illustrates a composition comprising effects pigments. The effects pigments are typically plate or plate-like pigment particles coated with thin layers of a secondary material with a higher refractive index. The compositions of the underlying plates are typically mica, synthetic mica, silica, or alumina. The coatings are typically titanium dioxide (typically anatase form), iron oxide, and bismuth oxychloride.

TABLE 9

| | Effect Pigment | | | | |
|---|---|---|---|---|---|
| | Uncoated | | Coated | | |
| | ΔE | Std. Dev. | ΔE | Std. Dev. | t-Test |
| White Effect Pigment | 4.85 | 1.68 | 0.39 | 0.11 | 5.30 |
| Green Effect Pigment | 2.97 | 1.41 | 0.42 | 0.22 | 3.57 |

The test was run at a concentration of 0.125 wt % effect pigment in a solution of 0.125 wt % DPPH in butoxy ethanol. The samples were irradiated at 0.35 W/m² UVA radiation for 20 minutes. Four duplicates of each sample were prepared. D-50 is measured in microns. In Table 9, the ΔE is significant when the t-test is 1.53 or greater.

TABLE 10

| | | Effect Pigment Size | | | |
|---|---|---|---|---|---|
| | | Uncoated | | Coated | |
| | | White Effect Pigment | Green Effect Pigment | White Effect Pigment | Green Effect Pigment |
| D-50 | Number | 15.45 | 14.13 | 16.30 | 14.62 |
| | Volume | 21.67 | 15.67 | 23.13 | 16.17 |

REFERENCES

EP 0761774
GB 785,393
GB 825,404
US 20060167138
US 20060210495
U.S. Pat. No. 3,024,126
U.S. Pat. No. 3,562,153
U.S. Pat. No. 3,647,742
U.S. Pat. No. 3,649,588
U.S. Pat. No. 3,920,865
U.S. Pat. No. 3,948,676
U.S. Pat. No. 4,061,503
U.S. Pat. No. 4,061,503
U.S. Pat. No. 4,068,024
U.S. Pat. No. 4,141,751
U.S. Pat. No. 4,233,366
U.S. Pat. No. 4,454,288
U.S. Pat. No. 4,644,077
U.S. Pat. No. 4,882,225
U.S. Pat. No. 5,277,888
U.S. Pat. No. 5,486,631
U.S. Pat. No. 5,536,492
U.S. Pat. No. 5,562,897
U.S. Pat. No. 5,565,591
U.S. Pat. No. 5,607,994
U.S. Pat. No. 5,631,310
U.S. Pat. No. 5,718,907
U.S. Pat. No. 5,756,788
U.S. Pat. No. 5,843,525
U.S. Pat. No. 5,959,004
U.S. Pat. No. 5,993,967
U.S. Pat. No. 6,022,404
U.S. Pat. No. 6,045,650
U.S. Pat. No. 6,086,668
U.S. Pat. No. 6,214,106
U.S. Pat. No. 6,500,415
U.S. Pat. No. 7,182,938
U.S. Pat. No. 7,438,836
WO 2009/131910
WO 95/23192

Jung K, Richter J, Kabrodt K, Lucke I M, Schellenberg I, Herrling T. The antioxidative power AP—A new quantitative time dependent (2D) parameter for the determination of the antioxidant capacity and reactivity of different plants. Spectrochim Acta A Mol Biomol Spectrosc. 63(2006):846-50.

Jung K, Sacher M, Blume G, Janßen F, Herrling T. How Active are Biocosmetic Ingredients? SÖFW-Journal 133 1/2-2007.

Andersch Björkman Y(1), Hagvall L, Siwmark C, Niklasson B, Karlberg A T, Bråed Christensson J. Air-oxidized linalool elicits eczema in allergic patients—a repeated open application test study. Contact Dermatitis. 2014 March; 70(3):129-38.

Jung K, Heinrich U, Tronnier H, Schnyder M, Herzog B, Herrling Th. High levels of free radicals in suncare products induce Acne Aestivalis in sensitive subjects. SÖFW/142 (2016): 2-8.

Wlàschek M et al. Solar UV irradiation and dermal photoaging. J Photochem Photobiol B. 2001 October; 63(1-3):41-51.

Wada et al., Mycosporine-Like Amino Acids and Their Derivatives as Natural Antioxidants. Antioxidants 2015, 4, 603-646.

Varahalaroa Vadlapudi, Antioxidant activities of marine algae: A review. Medicinal Plants as Antioxidant Agents: Understanding Their Mechanism of Action and Therapeutic Efficacy, 2012: 189-203 ISBN: 978-81-308-0509-2.

What is claimed is:

1. A coated powder, comprising:
    (a) particles, and
    (b) a coating, on the surface of the particles, including
        (1) silica moieties,
        (2) organo oxysilane moieties selected from the group consisting of mono-organo oxysilane moieties, bi-organo oxysilane moieties and tri-organo oxysilane moieties, and
        (3) poly(dialkyl)siloxane moieties,
    wherein the amount by weight in $SiO_2$ equivalents of the organo oxysilane moieties and the silica moieties is at least 0.0625% of the total coated powder weight per m²/g of the specific surface area of the particle to be coated,
    the particles comprise at least one oxide selected from the group consisting of ZnO, $TiO_2$ and mixtures thereof, and
    the coated powder is super-photostable.

2. The coated powder of claim 1, wherein the particles have an average particle size of 15-150 nm.

3. The coated powder of claim 2, wherein the organo oxysilane contains propylsilane moieties and the poly(dialkyl)siloxane comprises polydimethylsiloxane.

4. The coated powder of claim 1, wherein the organo oxysilane moieties each have the formula $R^1{}_n SiO_{4-n}$, with n=1, 2 or 3, and each $R^1$ group is independently selected from the group consisting of alkyl, alkenyl, alkynyl, aryl and heterocyclic radical.

5. The coated powder of claim 1, wherein the poly (dialkyl) siloxane moieties each have the formula $O(SiR^2{}_2)(R^2{}_2SiO)_n(SiR^2{}_2)O$ or $O(SiR^2{}_2)(R^2{}_2SiO)_n(SiR^2{}_2)OR^c$, where n is an integer of 2 to 14, each $R^2$ group is an alkyl, and $R^c$ is selected from the group consisting of H, methyl, ethyl and propyl.

6. A dispersion, comprising:
(1) the coated powder of claim 1,
(2) a fluid, and
(3) optionally an antioxidant.

7. The dispersion of claim 6, comprising the antioxidant.

8. The dispersion of claim 7, wherein the antioxidant is selected from the group consisting of vitamins, antioxidant minerals, antioxidant proteins, antioxidant enzymes and coenzymes, phytonutrients and antioxidant hormones.

9. The dispersion of claim 7, wherein the antioxidant is selected from the group consisting of ascorbic acid, tocopherol, green tea extract, hydroxytyrosol and quercetin dehydrate.

10. The dispersion of claim 6, further compprising a dispersing aid.

11. The dispersion of claim 10, wherein the dispersing aid is selected from the group consisting of stearic acid, stearates, palmitic acid, palmitates, oleic acid, oleates, polyhydroxy stearic acid, phosphate esters, linear alkyl substituted amines, triglycerol esters, polyethylene glycerol esters and mixtures thereof.

12. A composition, comprising the coated powder of claim 1 and an antioxidant.

13. A water-in-oil or oil-in-water emulsion, comprising the coated powder of claim 1, and a liquid carrier.

14. A composition comprising the coated powder of claim 1, and a resin.

15. A process for producing the coated powder of claim 1, comprising coating particles with a polymer, by polymerizing a composition, comprising
(i) the particles,
(ii) a first alkoxy silane selected from the group consisting of a tetra-alkoxy silane, a poly(tetra-alkoxy silane) and mixtures thereof,
(iii) an organo alkoxysilane selected from the group consisting of mono-organo alkoxysilane, bi-organo alkoxysilane, tri-organo alkoxysilane and mixtures thereof, and
(iv) a second alkoxy silane selected from the group consisting of a poly(dialkyl)siloxane and mixtures thereof.

16. A method of protecting skin from light, comprising coating skin with a composition comprising the coated powder of claim 1.

17. A method of protecting keratinous material comprising coating the keratinous material with a composition comprising the coated powder of claim 1.

18. A method of suppressing lipid peroxidation comprising applying to the skin a composition comprising the coated powder of claim 1.

19. A method of protecting antioxidants, comprising mixing an antioxidant with the coated powder of claim 1.

* * * * *

UNITED STATES PATENT AND TRADEMARK OFFICE
CERTIFICATE OF CORRECTION

PATENT NO. : 10,590,278 B2
APPLICATION NO. : 15/483669
DATED : March 17, 2020
INVENTOR(S) : Harry W. Sarkas et al.

It is certified that error appears in the above-identified patent and that said Letters Patent is hereby corrected as shown below:

In the Specification

In the Detail Description:
Column 10, Line 36, please delete "$R^cO(SiR^2_2)(R^2_2SiO)_n(SiR^2_2)OR^c$," and insert
--$R^cO(R^2_2SiO)_n(SiR^2_2)OR^c$,--
Column 10, Line 53, please delete "$O(SiR^2_2)(R^2_2SiO)_n(SiR^2_2)O$ or $O(SiR^2_2)(R^2_2SiO)_n(SiR^2_2)OR^c$" and insert --$O(R^2_2SiO)_n(SiR^2_2)O$ or $O(R^2_2SiO)_n(SiR^2_2)OR^c$--

In the Claims

Column 26, Lines 63 and 64, please delete "$O(SiR^2_2)(R^2_2SiO)_n(SiR^2_2)O$ or $O(SiR^2_2)(R^2_2SiO)_n(SiR^2_2)OR^c$," and insert --$O(R^2_2SiO)_n(SiR^2_2)O$ or $O(R^2_2SiO)_n(SiR^2_2)OR^c$,--

Signed and Sealed this
Thirty-first Day of August, 2021

Drew Hirshfeld
*Performing the Functions and Duties of the
Under Secretary of Commerce for Intellectual Property and
Director of the United States Patent and Trademark Office*